(12) United States Patent
Purdon et al.

(10) Patent No.: US 11,786,132 B2
(45) Date of Patent: Oct. 17, 2023

(54) SYSTEMS AND METHODS FOR PREDICTING AROUSAL TO CONSCIOUSNESS DURING GENERAL ANESTHESIA AND SEDATION

(71) Applicant: The General Hospital Corporation, Boston, MA (US)

(72) Inventors: Patrick L. Purdon, Somerville, MA (US); Oluwaseun Akeju, Dorchester, MA (US); Emery N. Brown, Brookline, MA (US)

(73) Assignee: The General Hospital Corporation, Boston, MA (US)

(*) Notice: Subject to any disclaimer, the term of this patent is extended or adjusted under 35 U.S.C. 154(b) by 850 days.

(21) Appl. No.: 16/657,194

(22) Filed: Oct. 18, 2019

(65) Prior Publication Data
US 2020/0046229 A1  Feb. 13, 2020

Related U.S. Application Data

(63) Continuation-in-part of application No. 16/165,580, filed on Oct. 19, 2018, and a continuation-in-part of
(Continued)

(51) Int. Cl.
*A61B 5/0205* (2006.01)
*A61B 5/00* (2006.01)
(Continued)

(52) U.S. Cl.
CPC ........... *A61B 5/0205* (2013.01); *A61B 5/369* (2021.01); *A61B 5/374* (2021.01); *A61B 5/4821* (2013.01);
(Continued)

(58) Field of Classification Search
None
See application file for complete search history.

(56) References Cited

U.S. PATENT DOCUMENTS 6,016,444 A   1/2000 John
6,067,467 A   5/2000 John
(Continued)

FOREIGN PATENT DOCUMENTS

JP    2008178546 A   8/2008
RU         95243 U1   6/2010
(Continued)

OTHER PUBLICATIONS

Ching et al., Thalamocortical Model for a Propofol-Induced α-rhythm Associated with Loss of Consciousness, Proceedings of the National Academy of Sciences, 2010, 107(52):22665-22670.
(Continued)

*Primary Examiner* — Michael R Bloch
(74) *Attorney, Agent, or Firm* — QUARLES AND BRADY LLP

(57) ABSTRACT

A system and method for monitoring a patient suspected of experiencing a state of unconsciousness are provided. In certain aspects, the method includes assembling physiological data, obtained from a plurality of sensors placed on a subject, into sets of time-series data, separating, from the sets of time-series data, a plurality of electroencephalogram signals, and determining, from the plurality of electroencephalogram signals, at least one of frequency information and amplitude information. The method can also include identifying, using the at least one of the frequency information and the amplitude information, spatiotemporal signatures indicative of a likelihood of arousing the patient to consciousness by applying an external stimulus and gener-
(Continued)

ating a report indicating the likelihood of arousing the patient to consciousness by applying the external stimulus.

14 Claims, 23 Drawing Sheets

Related U.S. Application Data application No. 15/504,542, filed as application No. PCT/US2015/046607 on Aug. 24, 2015, now abandoned, said application No. 16/165,580 is a continuation of application No. 14/115,682, filed as application No. PCT/US2012/036854 on May 7, 2012, now abandoned.

(60) Provisional application No. 62/040,844, filed on Aug. 22, 2014, provisional application No. 61/483,483, filed on May 6, 2011.

(51) Int. Cl.
*A61B 5/369* (2021.01)
*A61B 5/374* (2021.01)
*G16H 50/20* (2018.01)
A61B 5/02 (2006.01)
A61B 5/38 (2021.01)

(52) U.S. Cl.
CPC .......... *A61B 5/7275* (2013.01); *G16H 50/20* (2018.01); *A61B 5/02* (2013.01); *A61B 5/38* (2021.01); *A61B 5/7264* (2013.01); *G06F 2218/00* (2023.01)

(56) References Cited

U.S. PATENT DOCUMENTS

| | | | |
|---|---|---|---|
| 6,631,291 B2 | 10/2003 | Viertio-Oja et al. | |
| 2004/0193068 A1* | 9/2004 | Burton ............... | A61B 5/4812 600/595 |
| 2006/0009733 A1 | 1/2006 | Martin | |
| 2007/0055114 A1* | 3/2007 | Viertio-Oja ............ | A61B 5/389 600/300 |
| 2007/0060831 A1 | 3/2007 | Le et al. | |
| 2010/0076333 A9 | 3/2010 | Burton et al. | |
| 2011/0015538 A1 | 1/2011 | Matthews, Jr. | |
| 2011/0119212 A1 | 5/2011 | De Bruin et al. | |
| 2011/0125046 A1 | 5/2011 | Burton et al. | |
| 2011/0295096 A1 | 12/2011 | Bibian et al. | |

FOREIGN PATENT DOCUMENTS

| | | |
|---|---|---|
| WO | 2004037114 A2 | 5/2004 |
| WO | 2012154701 A1 | 11/2012 |

OTHER PUBLICATIONS

Cimenser et al., Developing New Neurophysiological Signatures of General Anesthesia Induced Loss of Consciousness, BMC Neuroscience, 2009, 10(1):P79, 2 pages.
Cimenser et al., Tracking Brain States Under General Anesthesia by Using Global Coherence Analysis, Proceedings of the National Academy of Sciences, 2011, 108(21):8832-8837.
Demanuele et al., Distinguishing Low Frequency Oscillations Within the 1/f Spectral Behaviour of Electromagnetic Brain Signals, Behavioral and Brain Functions, 2007, 3(1):1-14.
John et al., Invariant Reversible QEEG Effects of Anesthetics, Consciousness and Cognition, 2001, 10(2):165-183.
Mitra et al., Chapter 7—Time Series Analysis, In "Observed Brain Dynamics", Oxford University Press, UK, 2007, pp. 184-216.
Molaee-Ardekani et al., Delta Waves Differently Modulate High Frequency Components of EEG Oscillations in Various Unconsciousness Levels, In 2007 29th Annual International Conference of the IEEE Engineering in Medicine and Biology Society, pp. 1294-1297.
Mukamel et al., Phase-Based Measures of Cross-Frequency Coupling in Brain Electrical Dynamics Under General Anesthesia, In 2011 Annual International Conference of the IEEE Engineering in Medicine and Biology Society, pp. 1981-1984.
Schroter et al., Spatiotemporal Reconfiguration of Large-Scale Brain Functional Networks During Propofol-Induced Loss of Consciousness, Journal of Neuroscience, 2012, 32(37):12832-12840.
Smith et al., Bayesian Analysis of Interleaved Learning and Response Bias in Behavioral Experiments, Journal of Neurophysiology, 2007, 97(3):2516-2524.
Wong et al., Robust Time-Varying Multivariate Coherence Estimation: Application to Electroencephalogram Recordings During General Anesthesia, In 2011 Annual International Conference of the IEEE Engineering in Medicine and Biology Society, pp. 4725-4728.
Wong et al., Bayesian Analysis of Trinomial Data in Behavioral Experiments and Its Application to Human Studies of General Anesthesia, In 2011 Annual International Conference of the IEEE Engineering in Medicine and Biology Society, pp. 4705-4708.
PCT International Search Report and Written Opinion, PCT/US2012/036854, dated Aug. 16, 2012, 6 pages.
PCT International Search Report and Written Opinion, PCT/US2015/046607, dated Nov. 24, 2015, 9 pages.

\* cited by examiner

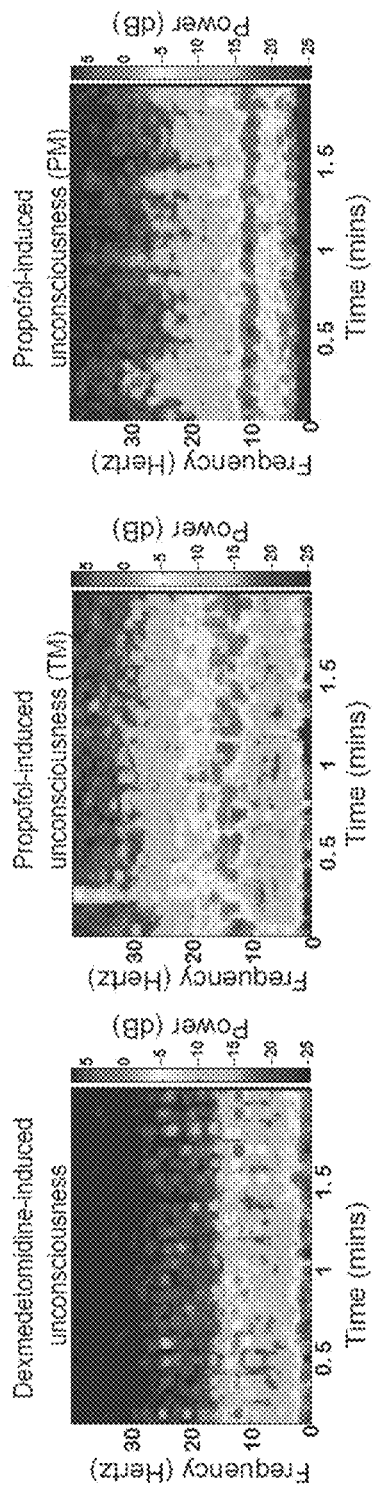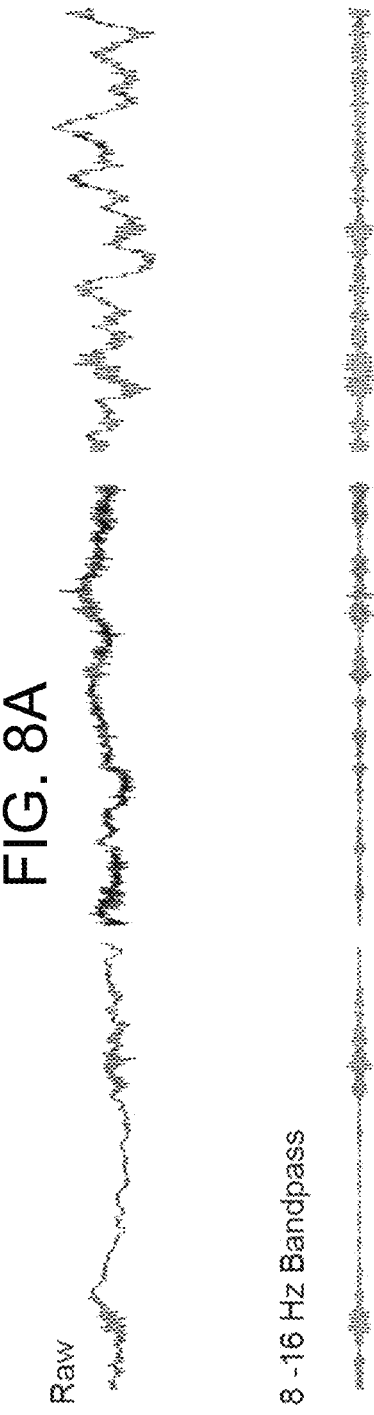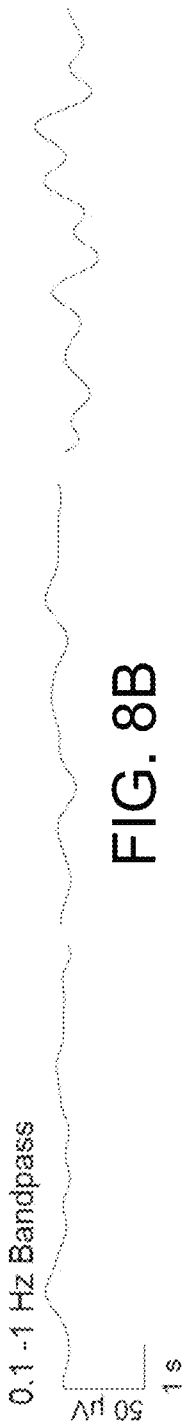
FIG. 8A
FIG. 8B

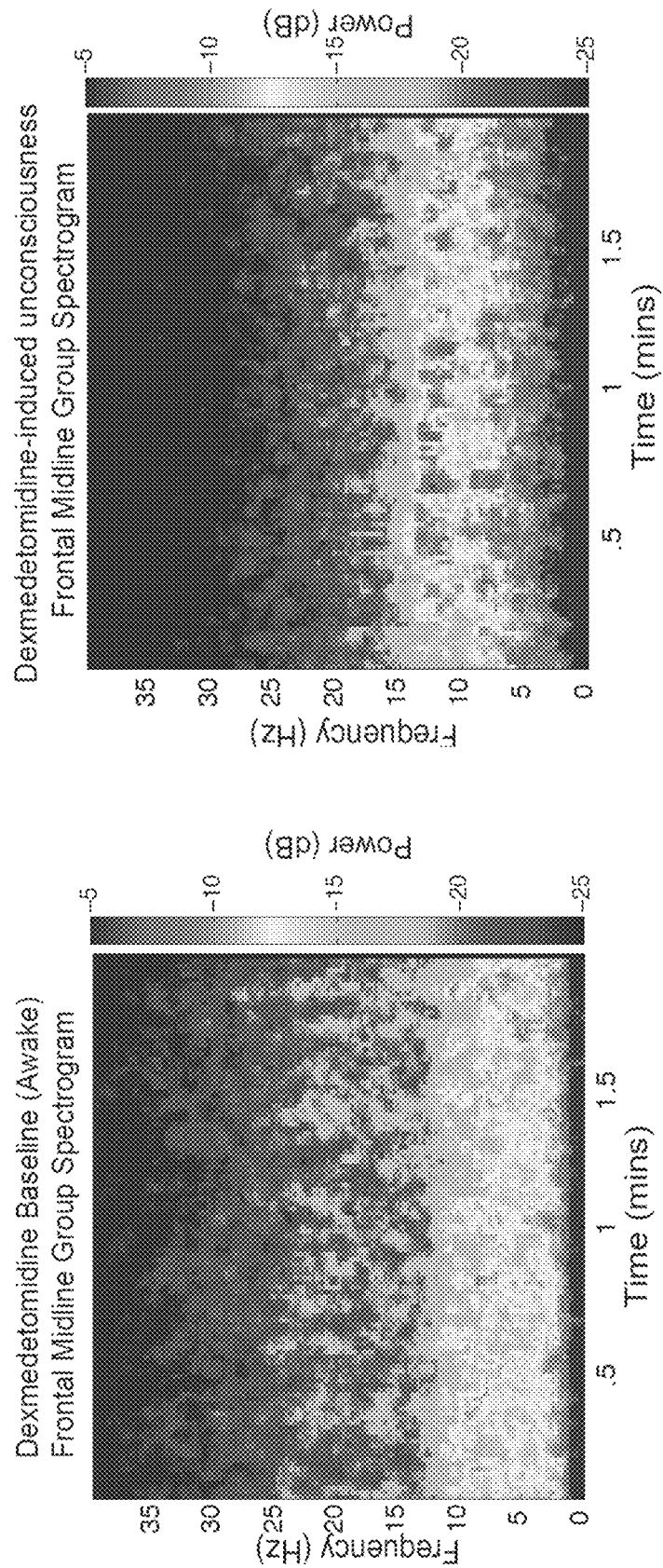

SYSTEMS AND METHODS FOR PREDICTING AROUSAL TO CONSCIOUSNESS DURING GENERAL ANESTHESIA AND SEDATION

CROSS-REFERENCE TO RELATED APPLICATIONS

This application is a continuation-in-part of U.S. application Ser. No. 15/504,542, filed Feb. 16, 2017, which is US National Stage of International Application No. PCT/US2015/046607 filed Aug. 24, 2015, which is based on, claims the benefit of, and incorporates herein by reference U.S. Provisional Application Ser. No. 62/040,844, filed Aug. 22, 2014. This application is also a continuation-in-part of U.S. application Ser. No. 16/165,580, filed Oct. 19, 2018, which is a continuation of U.S. application Ser. No. 14/115,682 filed Feb. 19, 2014, which is the US National Stage of International Application No. PCT/US2012/036854, filed May 7, 2012, which is based on, claims the benefit of, and incorporates herein by reference U.S. Provisional Application Ser. No. 61/483,483, filed May 6, 2011.

STATEMENT REGARDING FEDERALLY SPONSORED RESEARCH

This invention was made with government support under DP2-OD006454, DP1-OD003646, TR01-GM104948, and T32GM007592 awarded by the National Institutes of Health. The government has certain rights in the invention.

BACKGROUND OF THE INVENTION

The present invention generally relates to systems and methods for monitoring and controlling a state of a subject and, more particularly, to systems and methods for monitoring and assessing a probability of a subject being aroused from an unconscious state by an external stimulus.

General anesthetic drugs induce a variety of states of altered arousal, ranging from sedation to varying levels of unconsciousness. In some cases, patients can be aroused to consciousness by sufficiently strong external stimuli, while in other cases, patients cannot be aroused. With some drugs, such as the powerful GABA-A agonist propofol, it is possible to induce both of these states of unconsciousness at different doses. With other drugs, such as dexmedetomidine, the typical doses used in the operating room or intensive care unit place patients in a state where they can be readily aroused by external stimuli. With existing monitoring technologies in anesthesiology and critical care, it is not possible to differentiate between unconscious and arousable states and unconscious and non-arousable states.

There exists a clear need for systems and methods to accurately monitor and quantify subject states and based thereon, provide systems and methods for assessing the probability of a subject responding to an external stimulus.

SUMMARY OF THE INVENTION

The present invention overcomes drawbacks of previous technologies by providing systems and methods for monitoring and controlling brain states related to the administration and control of anesthetic compounds, using measures of brain activity. In some aspects, systems and methods described herein may be used to determine a likelihood of arousal to external stimuli.

In one aspect of the disclosure, a system for monitoring a patient suspected of experiencing a state of unconsciousness is provided. The system can include at least one sensor and at least one processor. The at least one sensor can be configured to acquire physiological data from the patient. The at least one processor can be configured to do one or more of the following: receive the physiological data from the at least one sensor; separate, from the physiological data, a plurality of electroencephalogram signals; determine, from the plurality of electroencephalogram signals, at least one of frequency information and amplitude information; identify, using the at least one of the frequency information and the amplitude information, spatiotemporal signatures indicative of a likelihood of arousing the patient to consciousness by applying an external stimulus; and generate a report indicating the likelihood of arousing the patient to consciousness by applying the external stimulus.

In another aspect of the present disclosure, a method for monitoring a patient suspected of experiencing a state of unconsciousness is provided. The method can include one or more of the following steps: positioning at least one sensor and the patient relative to one another, the at least one sensor configured to acquire physiological data from the patient; receiving, at a processor, the physiological data from the at least one sensor; identifying, using the processor and the physiological data, a plurality of electroencephalogram signals; determining, using the processor and the plurality of electroencephalogram signals, at least one of frequency information and amplitude information; identifying, using the processor and at least one of the frequency information and the amplitude information, spatiotemporal signatures indicative of a likelihood of arousing the patient to consciousness by applying an external stimulus; and generating a report indicating the likelihood of arousing the patient by applying the external stimulus.

The foregoing and other advantages of the disclosure will appear from the following description. In the description, reference is made to the accompanying drawings which form a part hereof, and in which there is shown by way of illustration a preferred embodiment of the disclosure. Such embodiment does not necessarily represent the full scope of the disclosure, however, and reference is made therefore to the claims and herein for interpreting the scope of the disclosure.

BRIEF DESCRIPTION OF THE DRAWINGS

The present disclosure will hereafter be described with reference to the accompanying drawings, wherein like reference numerals denote like elements.

FIG. 8A shows representative spectrograms of dexmedetomidine-induced unconsciousness, propofol-induced unconsciousness (TM), and propofol-induced unconsciousness (PM).

FIG. 8B shows representative traces of raw and filtered data corresponding to the data in FIG. 8A.

FIG. 9A is a group level spectrogram of dexmedetomidine baseline, as described in Example 1.

FIG. 9B is a group level spectrogram of dexmedetomidine-induce unconsciousness, as described in Example 1.

DETAILED DESCRIPTION

Figure 1A:
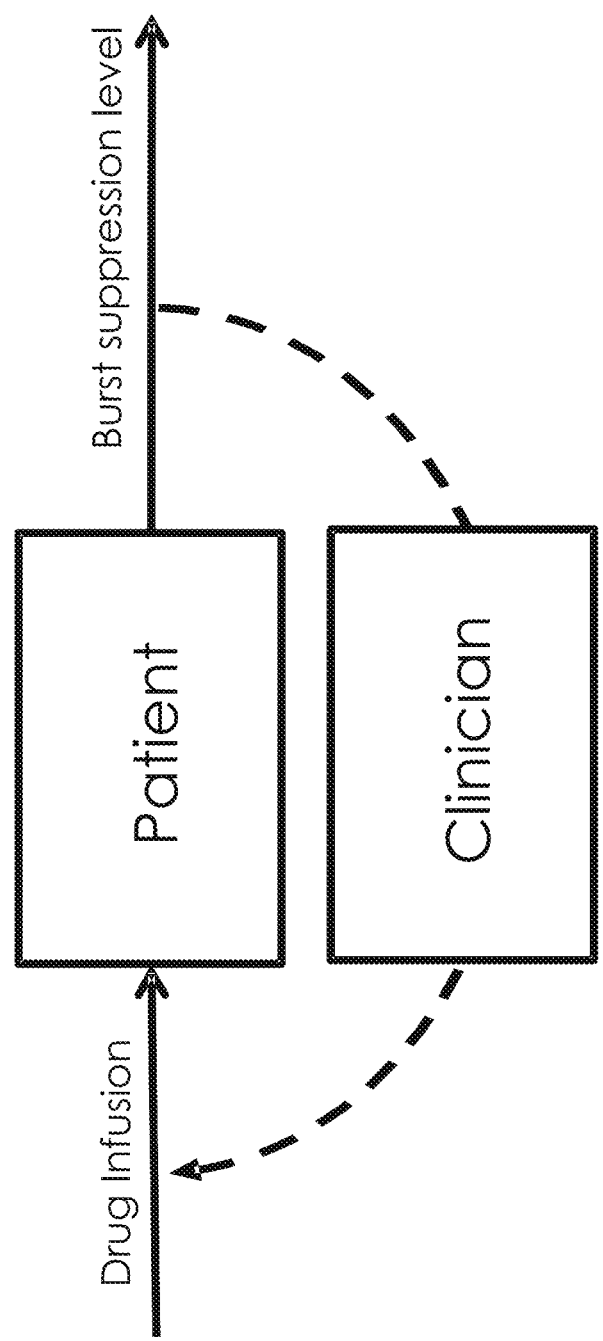
FIG. 1A is a schematic block diagram of a traditional anesthetic compound monitoring and control system that depends completely upon a clinician.

Despite major advances in identifying common molecular and pharmacological principles that underlie anesthetic drugs, it is not yet clear how actions at different molecular targets affect large-scale neural dynamics to produce unconsciousness. As such, anesthesiologists are typically trained to recognize the effects of anesthesia and extrapolate an estimate of the "level" of anesthetic influence on a given patient based on the identified effects of the administered anesthesia.

Using proprietary algorithms that combine spectral and entropy measurements, monitoring systems typically provide feedback through partial or amalgamized representations of the acquired signals. For example, many systems quantify the physiological responses of the patient receiving the dose of anesthesia and, thereby, convey the patient's depth of anesthesia, through a single dimensionless index. However, indices currently utilized generally relate indirectly to the level of consciousness, and given that different drugs act through different neural mechanisms, and produce different electroencephalogram ("EEG") signatures, associated with different altered states of consciousness, such approaches may be qualitative at best. Consequently, some EEG-based depth of anesthesia indices have been shown to poorly represent a patient's brain state, and moreover show substantial variability in underlying brain state and level of awareness at similar numerical values within and between patients. Not surprisingly, compared to non depth-of-anesthesia monitor based approaches, these monitors have been ineffective in reducing the incidence of intra-operative awareness.

In practice, one common process that clinicians use is to monitor EEG display to identify indications of "burst suppression." Burst suppression is an example of an EEG pattern that can be observed when the brain has severely reduced levels of neuronal activity, metabolic rate, and oxygen consumption. For example, burst suppression is commonly seen in profound states of general anesthesia. One example of a profound state of a patient under general anesthesia is medical coma. The burst suppression pattern often manifests as periods of bursts of electrical activity alternating with periods during which the EEG is isoelectric or suppressed. A variety of clinical scenarios require medical coma for purposes of brain protection, including treatment of uncontrolled seizures—status epilepticus—and brain protection following traumatic or hypoxic brain injury, anoxic brain injuries, hypothermia, and certain developmental disorders. Burst suppression represents a specific brain state resulting from such injuries, disorders, or medical interventions.

Traditional systems and methods that attempt to quantify burst suppression proceeds in two steps. First, characteristics of burst suppression are identified in the acquired data and the burst and suppression events are segregated or separated from EEG artifacts by conversion into a binary time-series format. Second, these systems and methods attempt to quantify the level of burst suppression. For example, some commercially available brain monitoring devices use a so-called "burst suppression ratio" ("BSR") as part of an algorithm to identify and track the state of burst suppression, where the BSR is a quantify related to the proportion of time, in a given time interval, that the EEG signal is designated as suppressed.

Although the importance of quantitatively analyzing burst suppression using, for example, a metric like BSR is broadly appreciated, in some instances, analyzing burst suppression by itself may not accurately indicate a state of consciousness. For example, even though binary values can be computed on intervals as short as 100 millisececonds or even every millisecond, it is not unusual to use several seconds of these binary values to compute the BSR. This assumes that the brain state remains stable throughout the period during which the BSR is being computed. When the level of brain activity is changing rapidly, such as with induction of general anesthesia, hypothermia, or with rapidly evolving disease states, this assumption may not hold true. Instead, the computation of the level of burst suppression should match the resolution at which the binary events are recorded. Unfortunately, this reflects a practical quandary for the algorithm designer. Namely, the design cannot calculate a BSR without a determined time interval, but the true interval would be best selected with knowledge of the BSR to be calculated.

To further compound the difficulties of using such BSR algorithms clinically, different manufactures use different segmentation algorithms to convert the EEG into a binary time-series. Accordingly, different devices from different manufactures produce different BSR estimates. Comparing results across devices/manufacturer's is often challenging. As a further clinical challenge, for any of the situations in which burst suppression is tracked quantitatively, an important objective is to make formal statistical comparisons at different points in time. However, the statistical properties of the BSR estimated by averaging the binary events over several second intervals have not been described. As a consequence, there is no principled way to use the current BSR estimates in formal statistical analyses of burst suppression. That is, there is a lack of formal statistical analyses and prescribed protocols to implement formal statistical analyses to be able to state with a prescribed level of certainty that two or more brain states differ using current BSR protocols.

The shortcomings of these monitoring systems is compounded by the fact that they are often used as the information source on which clinicians make decisions. For example, referring to FIG. 1A, a simplified schematic is illustrated showing that a "drug infusion" including a dose of anesthesia is delivered to a patient. Feedback from the patient is gathered by a monitoring system such as described above that attempts to identify and quantify burst suppression by providing an indication of "burst suppression level". The "burst suppression level" is generally the amount of burst suppression perceived by the clinician looking at the monitor display. This "burst suppression level" then serves as the input to a clinician that serves as the control of a feedback loop by adjusting the drug infusion levels based on the indicated "burst suppression level." This simplified example illustrates that errors or general inaccuracies in the "burst suppression level" indicated by the monitoring system and/or erroneous interpretations or assumptions by the clinician can exacerbate an already inexact process of controlling the drug infusion process. Such imprecision may be tolerable in some situations, but is highly unfavorable in others.

For example, in some clinical settings, it may be desirable to place a patient in a so-called "medical coma." To do so, burst suppression is induced by manually tuning drug infusion to meet certain specifications. Control of these infusions requires the nursing staff to monitor, frequently by eye, the infusion pump and the EEG waveform, and to titrate the infusion rate of the anesthetic drug to achieve and maintain the desired EEG pattern. It is impractical for the nursing staff to provide a continuous assessment of the EEG waveform in relation to the rate of drug infusion in such a way to maintain tight control of the patient's desired brain state.

Figure 1B:
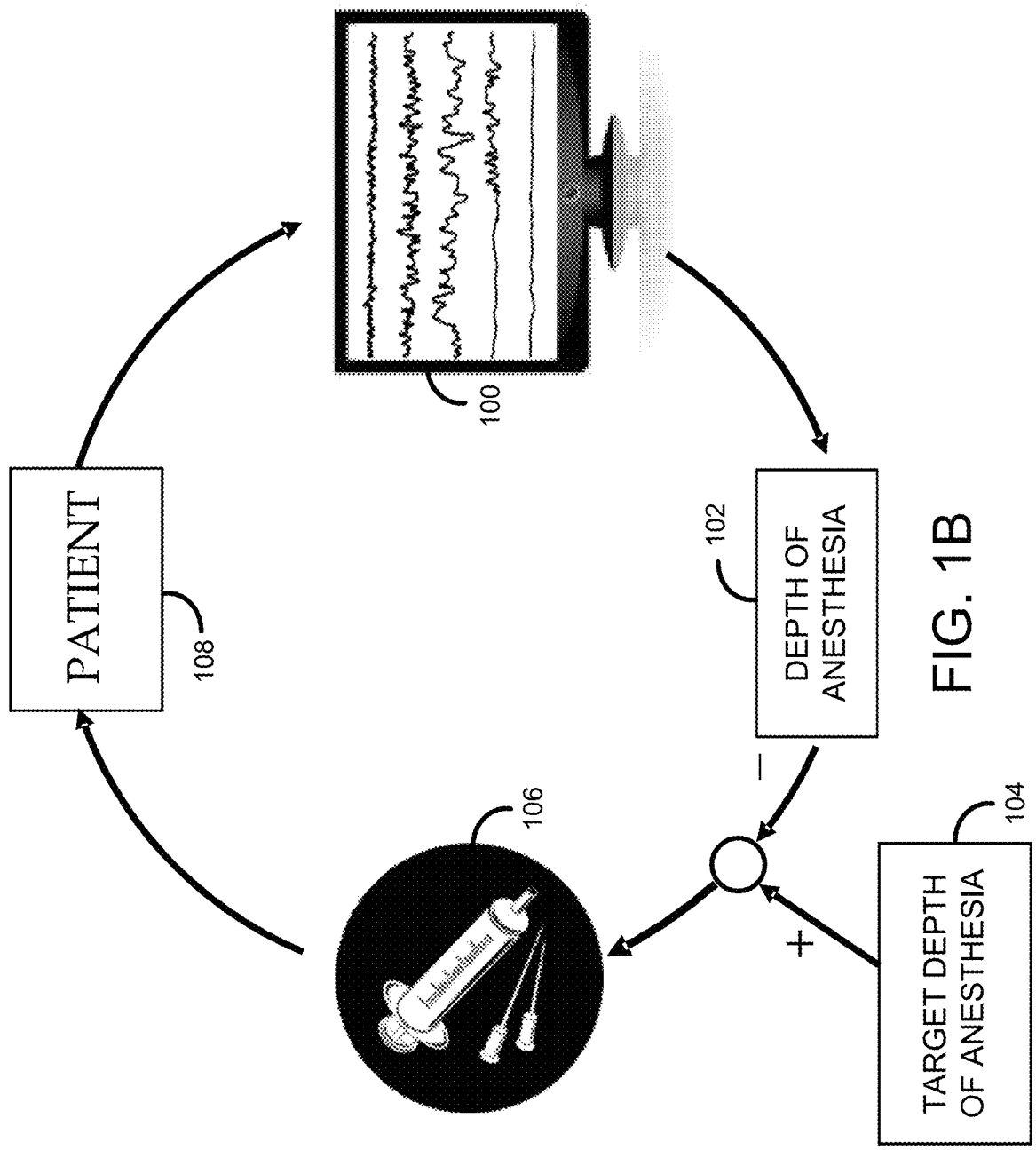
FIG. 1B is a schematic illustration of a traditional closed-loop anesthesia delivery (CLAD) system.

With these clinical challenges recognized, some have attempted to develop feedback and control systems to aid the clinician. For example, Bickford proposed an EEG-based, closed loop anesthetic delivery ("CLAD") system more than 60 years ago. For example, a simplified schematic diagram of an early CLAD system is provided in FIG. 1B. Bickford's original CLAD system of the 1950s used EEG content 100 in specific frequency bands as the control signal that indicated a current "depth of anesthesia" 102. The depth of anesthesia 102 was compared to a "target depth of anesthesia" 104, which determined with the drug infusion 106 should be increased or decreased. As such, a closed loop system was proposed to control the anesthetic delivered to the patient 108.

Later incarnations of the proposed CLAD systems used more sophisticated EEG analysis. For example, instead of simply relying on specific frequency bands as the control signal, systems were proposed that used metrics, such as the median frequency and the spectral edge, or the 50th and 95th quantiles of the power spectrogram, respectively. Studies observed a strong relationship between frequency content and its associated range and the corresponding depth of general anesthesia. Other possible control signals that were proposed included evoked potentials, or physiological responses, such as heart rate and blood pressure. Though commercial development of such systems did not begin in earnest until the 1980's, there have now been many clinical studies on the use of CLAD systems in anesthesiology practice and a system for sedation not using EEG is now commercially available.

Although CLAD systems have been around for many years and they are now used in anesthesiology practice outside of the United States, recent reports suggest that several problems with these systems have not been fully addressed. First, it has been recognized since 1937 that EEG patterns can serve as an indicator of brain state under general anesthesia. To date, sufficiently detailed quantitative analyses of the EEG waveform have not been performed to produce well-defined markers of how different anesthetic drugs or combinations of drugs alter the states of the patient and how such variations manifest in EEG waveforms and other physiological characteristics.

In an attempt to combat such problems, the so-called Bispectral Index ("BIS") has been used an EEG-based marker to track brain state under general anesthesia and to provide a control signal for CLAD systems. BIS is derived by computing spectral and bispectral features of the EEG waveform. The features are input to a proprietary algorithm to derive an index between 0 and 100, in which 100 correspond to fully awake state with no drug effects and 0 corresponds to the most profound state of coma. As referenced above, BIS often serves as a common, single indicator clinicians rely upon to interpret the data acquired by a monitoring system. That is, clinicians simply rely upon the BIS indication to make clinical decisions.

As a control signal, BIS can inherently have only limited success, as the same BIS value can be produced by multiple distinct brain states. A patient under general anesthesia with isoflurane and oxygen, a patient sedated with dexmedetomidine, and a patient in stage III, or slow-wave, sleep can all have BIS values in the 40-to-60 range, which is the BIS interval in which surgery is conducted. Of these three patients, only the first is most likely in a state of "general anesthesia" and appropriate for conducting surgery. In this context, "general anesthesia" refers to unconsciousness, amnesia, analgesia, akinesia with maintenance of physiological stability. Similarly, patients anesthetized with ketamine alone or in combination with other anesthetic agents show high BIS values suggesting an awake or lightly sedated state, despite being in a state of general anesthesia. Although most reports nonetheless claim successful brain state control, such control has not been reliably demonstrated in studies involving individual subjects or real-time implementations.

Second, using BIS to account for individual variability in response to anesthetic drugs and hence, in EEG patterns, under normal, surgical, and intensive care unit conditions is a challenge. Third, EEG processing by commercially-available monitors of anesthetic state is performed, not in real-time, but with a 20-to-30-second delay. By contrast, coherence and synchrony methods provided herein, as will be described, may require only the length of time to acquire one window of data, for instance 4 seconds, followed by a short processing time much less than 1 second. Fourth, CLAD systems use ad-hoc algorithms instead of formal deterministic or stochastic control paradigms in their design. As a consequence, the reports in which CLAD systems have been implemented do not show reliable repeatable control results. Indeed, to give the appearance of successful control, the results of several subjects are often averaged in plots of CLAD performance. Finally, some have proposed the theoretical use of established control principles to design a CLAD system. However, such proposals have suggested the derivation of a wavelet-based index of anesthetic depth from the EEG, which fundamentally proposes a control signal that is analogous to BIS. Simply, until more is known about the neurophysiology of how EEG patterns relate to brain states under general anesthesia, developing generally applicable CLAD systems is a challenging problem. To this point, as described above, metrics such as BSR suffer from similar limitations and, thus, have not been suitable for developing generally applicable CLAD systems for at least the reasons discussed above.

Perhaps recognizing the complex nature of the EEG waveform and the shortcomings of BIS as a control system, Vijn and Sneyd designed CLAD systems for rats using a different metric, namely BSR, as the control signal. BSR, is defined as the proportion of time per epoch that the EEG is suppressed below a predetermined voltage threshold. The BSR ranges from 0, meaning no suppression, to 1, meaning an isoelectric EEG. The objective of such investigation was to develop a model-free approach to CLAD-system design to determine if performance of new drugs in a CLAD system could provide useful information on drug design. They processed their error signal using a non-standard deterministic control strategy that was the product of a proportional and an integral term. Although the authors claim that their CLAD system maintained control of BSR for both propofol and etomidate, they reported BSR time courses averaged over groups of rats and not for individual animals. The Vijn and Sneyd CLAD system was recently implemented by Cotten et al. to test the efficacy of new etomidate-based anesthetics in controlling BSR in rats. These authors also reported only average time courses. Accordingly there seems to be a lack of studies on the use of CLAD systems to control burst suppression in human experiments or in the ICU to maintain a level of medical coma.

To further complicate matters, there are a great number of variables that can influence the effects, effectiveness, and, associated therewith, the "level" of anesthetic influence on a given patient. Thus, closed-loop control systems can fail if the drug infusion does not account for any of the plethora of variables. Some variables include physical attributes of the patient, such as age, state of general health, height, or weight, but also less obvious variables that are extrapolated, for example, based on prior experiences of the patient when under anesthesia. When these variables are compounded with the variables of a given control system or method and the variables presented by a particular anesthetic compound or, more so, combination of anesthetic compounds, the proper and effective administration of anesthesia to a given patient can appear to be an art, rather than a science.

In addition, whether controlled by a system, such as a CLAD system, or a more traditional clinician-specific control, emergence from general anesthesia is a slow passive process achieved simply by allowing the effects of the drug to wear off. Emergence from anesthesia is traditionally a passive process whereby anesthetic drugs are merely discontinued at the end of surgery, and no drugs are administered to actively reverse their effects on the brain and central nervous system. That is, the general anesthetic agents are merely discontinued at the end of surgery, leaving the anesthesiologist and surgeon to wait for the patient to recover consciousness. The timing of emergence can be unpredictable because many factors including the nature and duration of the surgery, and the age, physical condition and body habits of the patient, can greatly affect the pharmacokinetics and pharmacodynamics of general anesthetics. Although the actions of many drugs used in anesthesiology can be pharmacologically reversed when no longer desired (e.g. muscle relaxants, opioids, benzodiazepines, and anticoagulants), this is not the case for general anesthetic induced loss of consciousness. While some basic ideas for actively reversing the effects of anesthesia have been considered, they do not translate well to traditional monitoring systems and control methods because these monitoring and control methods are generally unidirectional. For example, using burst-suppression based metrics for determining an increasing state of consciousness is counterintuitive, at best. Not surprisingly, then, control algorithms have not been developed to facilitate actively controlled recovery.

None of the aforementioned systems or methods include a capability to quantify the likelihood that a patient can be aroused by an external stimulus.

As will be described, the present disclosure overcomes drawbacks of previous technologies and provides systems and methods for monitoring and controlling a state of a patient suspected of experiencing a state of unconsciousness.

Figure 2A:
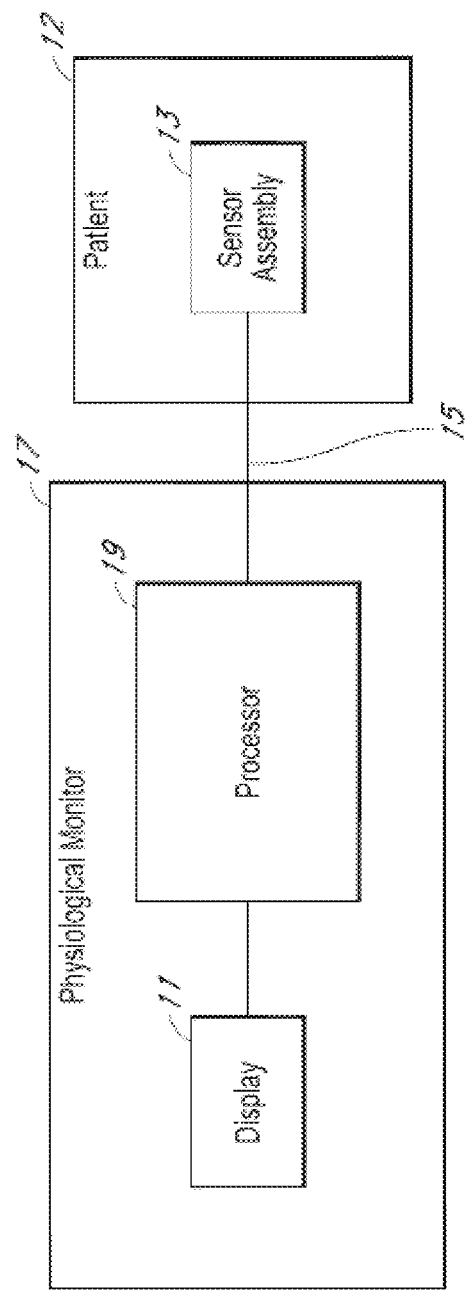
FIG. 2A is a block diagram of an example monitoring and control system in accordance with the present disclosure.
Figure 2B:
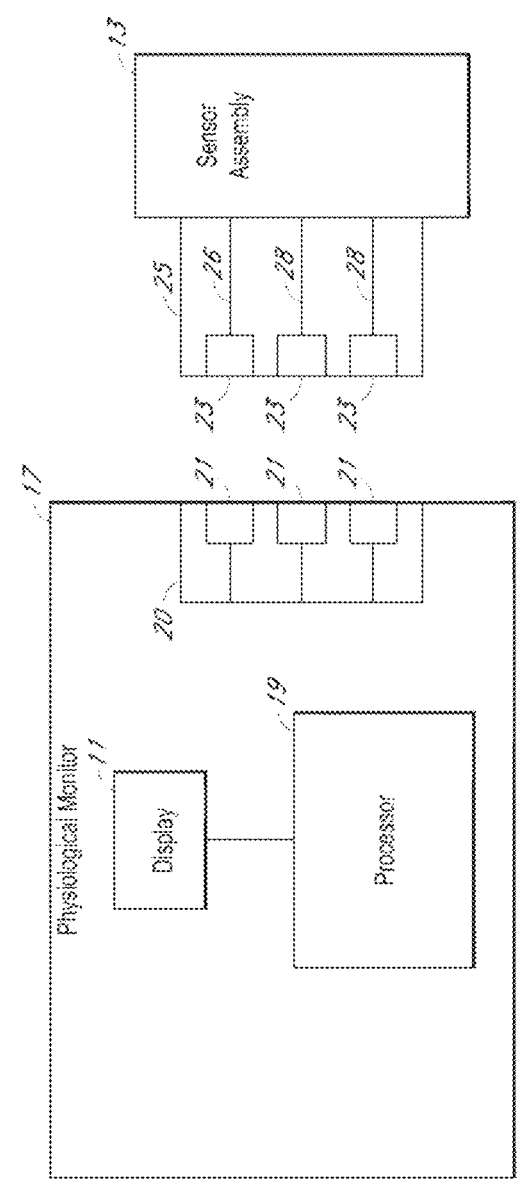
FIG. 2B is a block diagram of an example monitoring and control system in accordance with the present disclosure.

Referring specifically to the drawings, FIGS. 2A and 2B depict block diagrams of example patient monitoring systems and sensors that can be used to provide physiological monitoring and control of a patient's state, such as consciousness state monitoring, with loss of consciousness or emergence detection.

For example, FIG. 2A shows an aspect of a physiological monitoring system 10. In the physiological monitoring system 10, a medical patient 12 is monitored using one or more sensors 13, each of which transmits a signal over a cable 15 or other communication link or medium to a physiological monitor 17. The physiological monitor 17 includes a processor 19 and, optionally, a display 11. The one or more sensors 13 include sensing elements such as, for example, electrical EEG sensors, or the like. The sensors 13 can generate respective signals by measuring various physiological parameters of the patient 12. The signals are then processed by one or more processors 19.

In some implementations, the one or more processors 19 may be configured to determine, from acquired electroencephalogram signals, information associated with particular frequencies or frequency ranges, including spectral amplitudes, phases, power, locations and so forth, describing the signals. The one or more processors 19 may then analyze the signals to identify, using such information, spatiotemporal signatures indicative of a likelihood of arousing the patient to consciousness by applying an external stimulus. In some aspects, the one or more processors 19 may be configured to utilize patient, as well as drug information in determining the likelihood of arousing the patient. For example, patients at a deeper level of propofol-induced anesthesia may be less likely to be aroused compared to patients at lower dose levels of propofol, as well as those under dexmedetomidine-induced anesthesia.

The one or more processors 19 may then communicate the processed signals and any information generated therefrom to the display 11 if a display 11 is provided. In an aspect, the display 11 is incorporated in the physiological monitor 17. In another aspect, the display 11 is separate from the physiological monitor 17. The monitoring system 10 is a portable monitoring system in one configuration. In another instance, the monitoring system 10 is a pod, without a display, and is adapted to provide physiological parameter data to a display.

For clarity, a single block is used to illustrate the one or more sensors 13 shown in FIG. 2A. It should be understood that the sensor 13 shown is intended to represent one or more sensors. In an aspect, the one or more sensors 13 include a single sensor of one of the types described below. In another aspect, the one or more sensors 13 include at least two EEG sensors. In still another aspect, the one or more sensors 13 include at least two EEG sensors and one or more brain oxygenation sensors, and the like. In each of the foregoing aspects, additional sensors of different types are also optionally included. Other combinations of numbers and types of sensors are also suitable for use with the physiological monitoring system 10.

In some aspects of the system shown in FIG. 2A, all of the hardware used to receive and process signals from the sensors are housed within the same housing. In other aspects, some of the hardware used to receive and process signals is housed within a separate housing. In addition, the physiological monitor 17 can include hardware, software, or both hardware and software, whether in one housing or multiple housings, used to receive and process the signals transmitted by the sensors 13.

As shown in FIG. 2B, the EEG sensor 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors, one or more additional cables 15 can be provided.

In some aspects, the ground signal is an earth ground, but in other aspects, the ground signal is a patient ground, sometimes referred to as a patient reference, a patient reference signal, a return, or a patient return. In some aspects, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another aspect, the sensor 13 and the physiological monitor 17 communicate wirelessly.

Figure 3A:
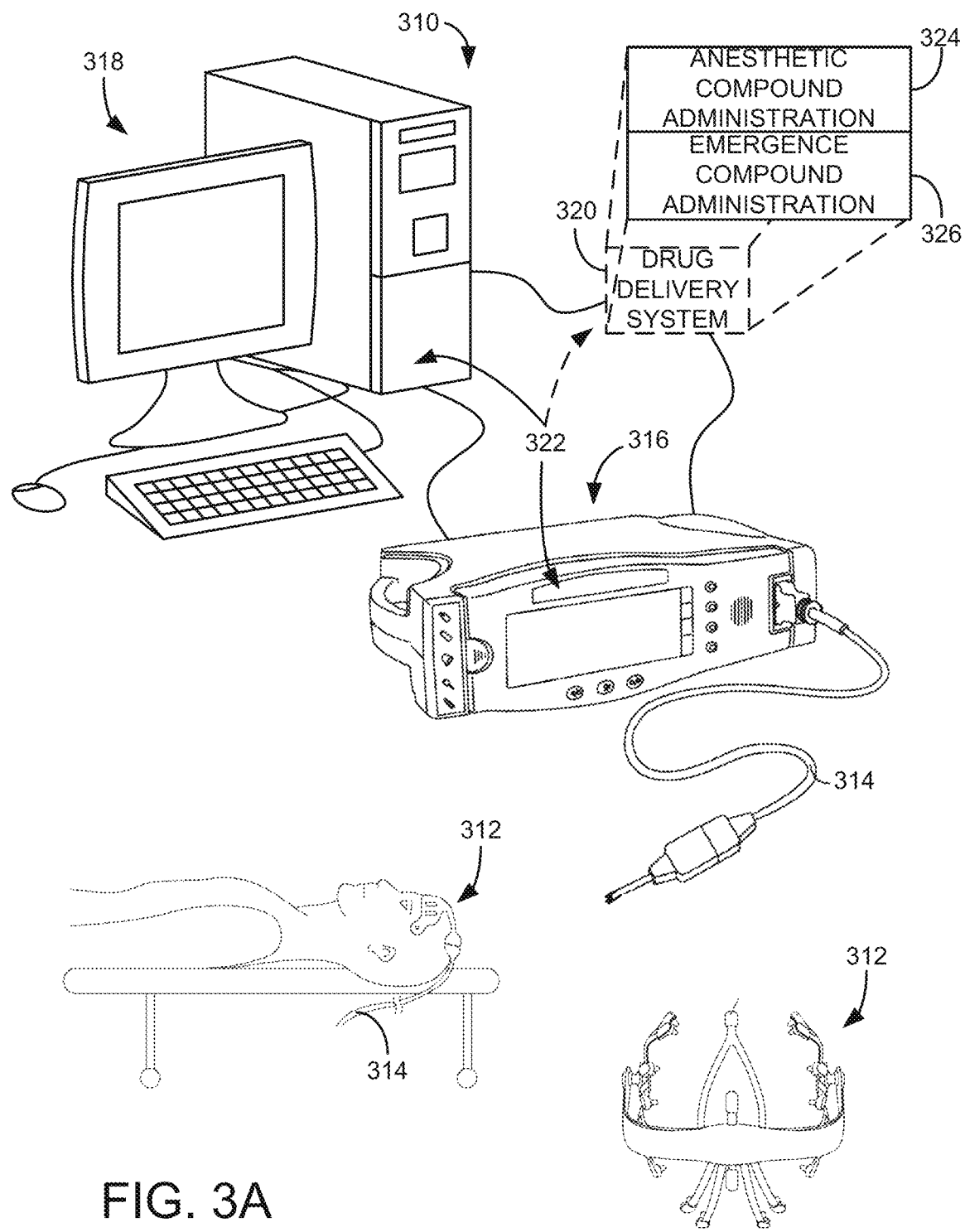
FIG. 3A is an illustration of an example monitoring and control system in accordance with the present disclosure.

Referring now to FIG. 3A, an example system 310 for monitoring and controlling a patient during and after administration of at least one drug having anesthetic properties is illustrated. The system 310 includes a patient monitoring device 312, such as a physiological monitoring device, illustrated in FIG. 3A as an electroencephalography (EEG) electrode array. However, it is contemplated that the patient monitoring device 312 may also include mechanisms for monitoring galvanic skin response (GSR), for example, to measure arousal to external stimuli or other monitoring system such as cardiovascular monitors, including electrocardiographic and blood pressure monitors, and also ocular Microtremor monitors. One specific realization of this design utilizes a frontal Laplacian EEG electrode layout with additional electrodes to measure GSR and/or ocular microtremor. Another realization of this design incorporates a frontal array of electrodes that could be combined in post-processing to obtain any combination of electrodes found to optimally detect the EEG signatures described earlier, also with separate GSR electrodes. Another realization of this design utilizes a high-density layout sampling the entire scalp surface using between 64 to 256 sensors for the purpose of source localization, also with separate GSR electrodes.

Figure 3B:
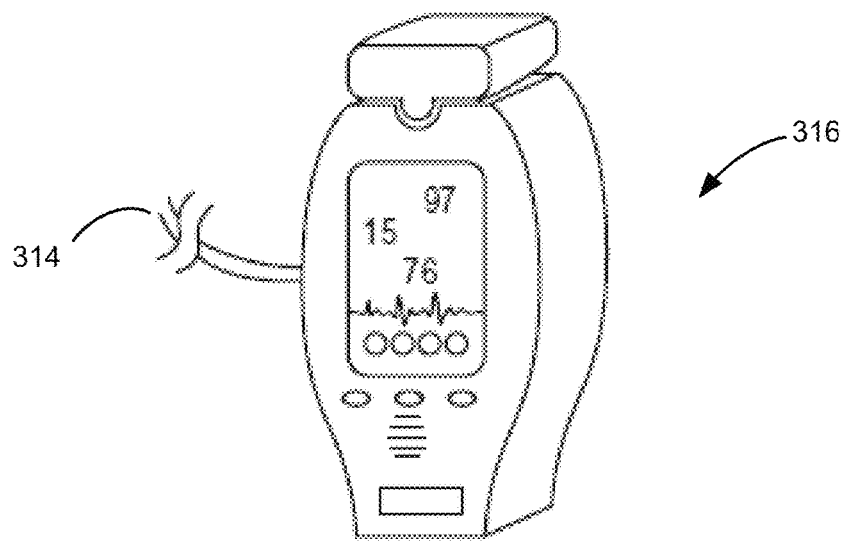
FIG. 3B is an illustration of an example portable monitoring system in accordance with the present disclosure.

The patient monitoring device 312 may be connected via a cable 314 to communicate with a monitoring system 316, which may be a portable system or device (as shown in FIG. 3B), and provides input of physiological data acquired from a patient to the monitoring system 316. Also, the cable 314 and similar connections can be replaced by wireless connections between components. As illustrated in FIG. 3A, the monitoring system 316 may be further connected to a dedicated analysis system 318. Also, the monitoring system 316 and analysis system 318 may be integrated.

The monitoring system 316 may be configured to receive raw signals acquired by the EEG electrode array and assemble, and even display, the raw signals as EEG waveforms. Accordingly, the analysis system 318 may receive the EEG waveforms from the monitoring system 316 and, as will be described, analyze the EEG waveforms and signatures therein based on a selected anesthesia compound, determine a state of the patient based on the analyzed EEG waveforms and signatures, and generate a report, for example, as a printed report or, preferably, a real-time display of signature information and determined state. However, it is also contemplated that the functions of monitoring system 316 and analysis system 318 may be combined into a common system. In one aspect, the monitoring system 316 and analysis system 318 may be configured to determine, based on frequency information and/or amplitude information, a likelihood of arousing a subject using an external stimulus.

In some configurations, the system 310 may also include a drug delivery system 320. The drug delivery system 320 may be coupled to the analysis system 318 and monitoring system 316, such that the system 310 forms a closed-loop monitoring and control system. Such a monitoring and control system in accordance with the present disclosure is capable of a wide range of operation, but includes user interfaces 322 to allow a user to provide any input or indications to configure the monitoring and control system, receive feedback from the monitoring and control system, and, if needed reconfigure and/or override the monitoring and control system.

Figure 3C:
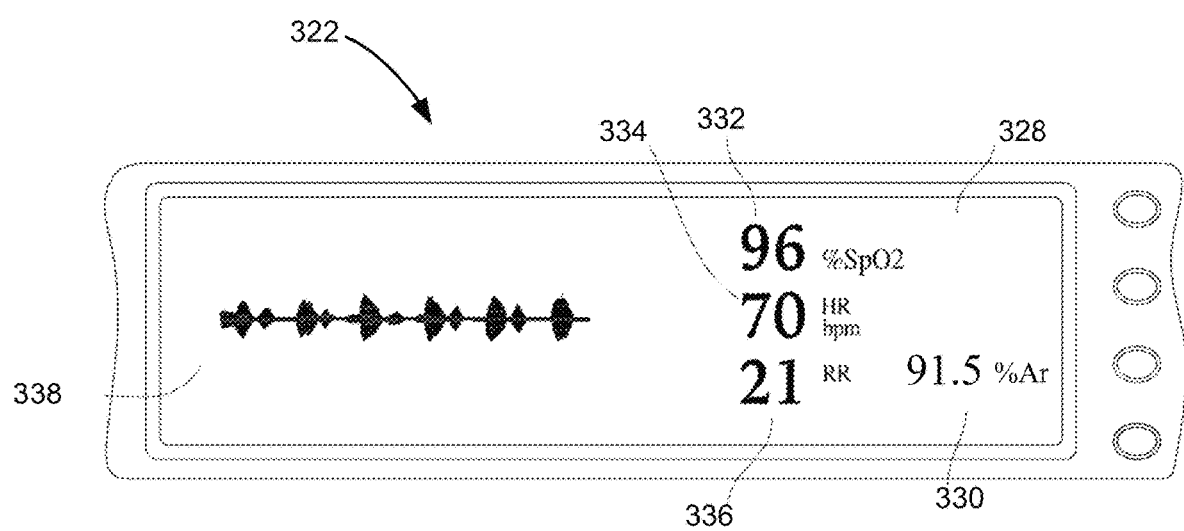
FIG. 3C is an illustration of an example display for the monitoring and control system of FIG. 3A

Referring specifically to FIG. 3C, a non-limiting example of a user interface 322 for a monitoring system 316 is illustrated, which may include a multiparameter physiological monitor display 328. For example, the display 328 can output a likelihood of arousal by an external stimulus indicator 330. The likelihood of arousal by an external stimulus indicator 330 can be generated using any of the techniques, as described. The display 328 may also provide parameter data using an oxygen saturation ("SpO$_2$") indicator 332, a pulse rate indicator 334, and a respiration rate indicator 336, any other indicator representative of any desired information. In the depicted aspect shown in FIG. 3C, the likelihood of arousal by an external stimulus indicator 330 includes text that indicates the likelihood that a patient can be aroused by an external stimulus. In some aspects, the likelihood of arousal by an external stimulus indicator 330 may include an index indicating numeric likelihood of arousal of the patient by external stimuli. The text displayed in the likelihood of arousal by an external stimulus indicator 330 may depend on a confidence calculation from one of the processes described above. Each one of the likelihood of arousal by an external stimulus detection processes described above may have different confidence rating depending on how accurately the particular process or combination of processes can predict a likelihood of arousal by an external stimulus. The confidence rating may be stored in the patient monitor. In some aspects, more than one of processes (described above) can be used to determine the likelihood of arousal by an external stimulus indicator 330. Furthermore, the display 328 can also provide any segment of raw or processed waveform signals 338 as output, including time-series EEG signals, intermittently or in real time.

Referring back to FIG. 3A, in some configurations, the drug delivery system 320 is not only able to control the administration of anesthetic compounds for the purpose of placing the patient in a state of reduced consciousness influenced by the anesthetic compounds, such as general anesthesia or sedation, but can also implement and reflect systems and methods for bringing a patient to and from a state of greater or lesser consciousness.

For example, in accordance with one aspect of the present disclosure, methylphenidate (MPH) can be used as an inhibitor of dopamine and norepinephrine reuptake transporters and actively induces emergence from isoflurane general anesthesia. MPH can be used to restore consciousness, induce electroencephalogram changes consistent with arousal, and increase respiratory drive. The behavioral and respiratory effects induced by methylphenidate can be inhibited by droperidol, supporting the evidence that methylphenidate induces arousal by activating a dopaminergic arousal pathway. Plethysmography and blood gas experiments establish that methylphenidate increases minute ventilation, which increases the rate of anesthetic elimination from the brain. Also, ethylphenidate or other agents can be used to actively induce emergence from isoflurane, propofol, or other general anesthesia by increasing arousal using a control system, such as described above.

Therefore, a system, such as described above with respect to FIG. 3A, can be provided to carry out active emergence from anesthesia by including a drug delivery system 320 with two specific sub-systems. As such, the drug delivery system 320 may include an anesthetic compound administration system 324 that is designed to deliver doses of one or more anesthetic compounds to a subject and may also include a emergence compound administration system 326 that is designed to deliver doses of one or more compounds that will reverse general anesthesia or enhance the natural emergence of a subject from anesthesia.

For example, MPH and analogues and derivatives thereof induces emergence of a subject from anesthesia-induced unconsciousness by increasing arousal and respiratory drive. Thus, the emergence compound administration system 326 can be used to deliver MPH, amphetamine, modafinil, amantadine, or caffeine to reverse general anesthetic-induced unconsciousness and respiratory depression at the end of surgery. The MPH may be dextro-methylphenidate (D-MPH), racemic methylphenidate, or leva-methylphenidate (L-MPH), or may be compositions in equal or different ratios, such as about 50%:50%, or about 60%:40%, or about 70%:30%, or 80%:20%, 90%:10%, 95%:5% and the like. Other agents may be administered as a higher dose of methylphenidate than the dose used for the treatment of Attention Deficit Disorder (ADD) or Attention Deficit Hyperactivity Disorder (ADHD), such as a dose of methylphenidate can be between about 10 mg/kg and about 5 mg/kg, and any integer between about 5 mg/kg and 10 mg/kg. In some situations, the dose is between about 7 mg/kg and about 0.1 mg/kg, or between about 5 mg/kg and about 0.5 mg/kg. Other agents may include those that are inhaled.

Figure 4:
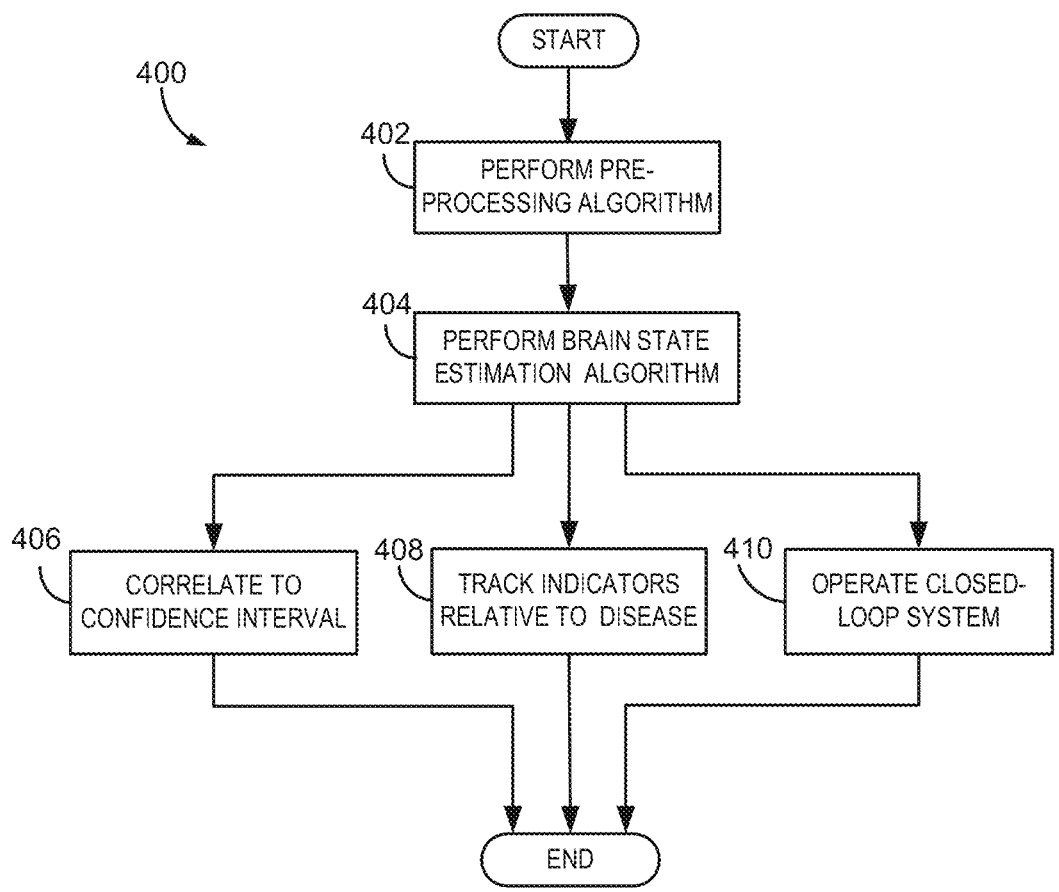
FIG. 4 is a flow chart setting forth the steps of a monitoring and control process in accordance with the present disclosure.

Turning now to FIG. 4, a process 400 for monitoring and controlling a state of a patient in accordance with the present disclosure begins at process block 402 by performing a pre-processing algorithm that analyzes waveforms acquired from an EEG monitoring system, as described. In some aspects, at process block 402, indicators related to the EEG waveforms may be identified, such as spike rates, burst suppression rates, oscillations (for example, slow or low-frequency oscillations in the range between 0.1 and 1 Hz and/or thalamocortical oscillations), power spectra characteristics, phase modulations, and so forth. At this step, raw EEG waveforms may be modified, transformed, enhanced, filtered, or manipulated to take any desired or required form, or possess any desired or required features or characteristics. The pre-processed data is then, at process block 404, provided as an input into a brain state estimation algorithm. In one aspect, the brain state estimation algorithm may perform a determination of current and/or future brain states related to measures of brain synchrony and/or coherence, under administration of any combination of anesthetic compounds, such as during general anesthesia or sedation.

The brain state estimation algorithm output, at process block 406, may be correlated with "confidence intervals." The confidence intervals are predicated on formal statistical comparisons between the brain state estimated at any two time points. Also, at process block 408, the output of the brain state estimation algorithm can be used to identify and track brain state indicators, such as spike rates, low-frequency oscillations, power spectra characteristics, phase modulations, and so forth, during medical procedures or disease states. Exemplary medically-significant states include hypothermia, general anesthesia, medical coma, and sedation to name but a few. The output of the brain state estimation algorithm may also be used, at process block 410 as part of a closed-loop anesthesia control process.

Figure 5A:
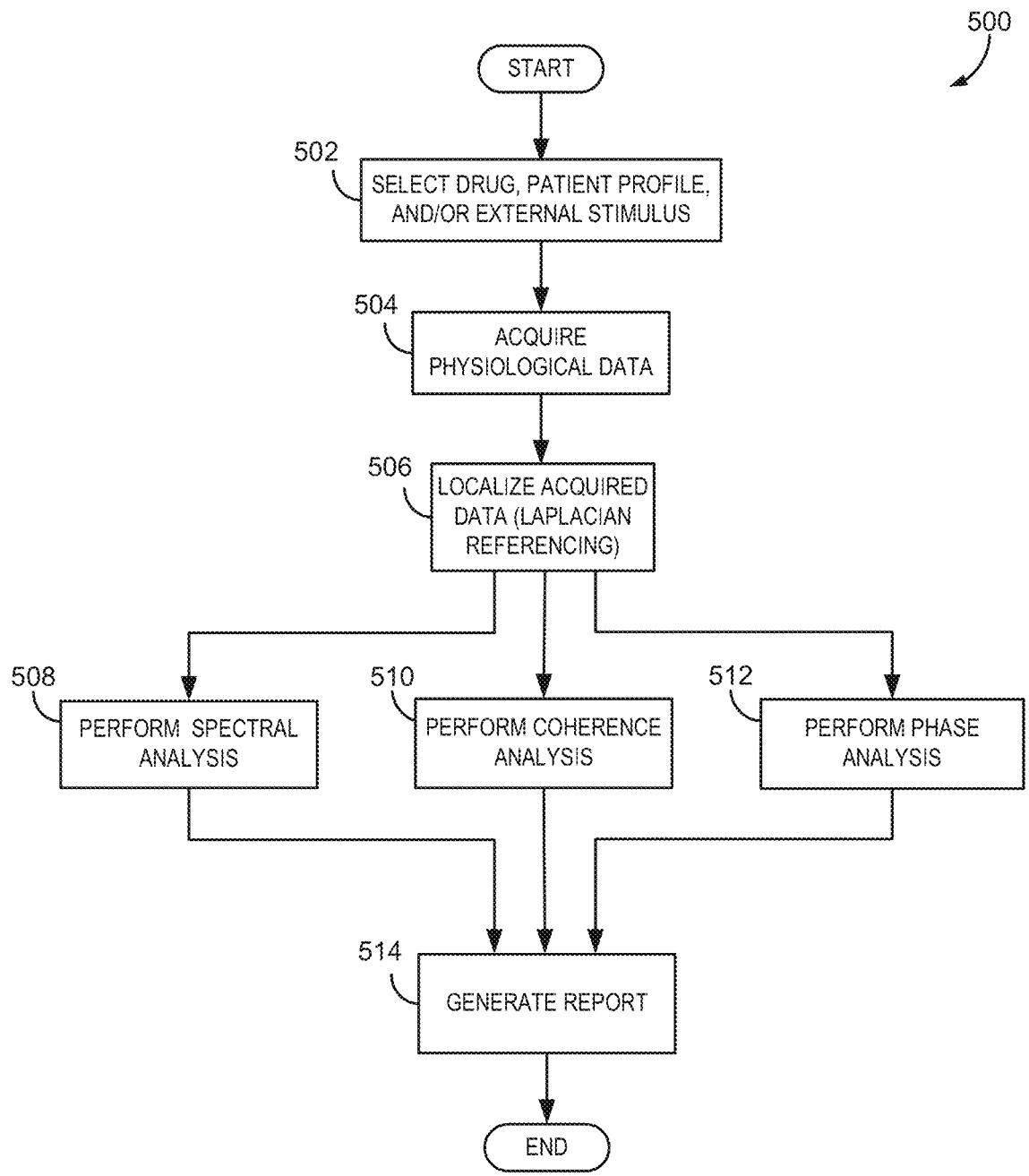
FIG. 5A is a flow chart setting forth steps of a process for determining a brain state of a patient, in accordance with the present disclosure.

Also, the present disclosure provides methods for determining a brain state of a patient, using systems as described. Referring now to FIG. 5A, a process 500 begins at process block 502 with the selection of a desired drug, such as anesthesia compound or compounds, and/or an indication related to a particular patient profile, such as a patient's age, height, weight, gender, or the like, and/or the desired external stimulus that is intended to be used to attempt to arouse the patient from unconsciousness. Furthermore, drug administration information, such as timing, dose, rate, and the like, in conjunction with the above-described EEG data may be acquired and used to estimate and predict future patient states in accordance with the present disclosure. As will be described, the present disclosure recognizes that the physiological responses to anesthesia vary based on the specific compound or compounds administered, as well as the patient profile. For example, elderly patients have a tendency to show lower amplitude alpha power under anesthesia, with some showing no visible alpha power in the unconscious state. The present disclosure accounts for this variation between an elderly patient and a younger patient. Furthermore, the present disclosure recognizes that analyzing physiological data for signatures particular to a specific anesthetic compound or compounds administered and/or the profile of the patient substantially increases the ability to identify particular indicators of the patient's brain being in a particular state and the accuracy of state indicators and predictions based on those indicators.

For example, the following drugs are examples of drugs or anesthetic compounds that may be used with the present disclosure: Propofol, Etomidate, Barbiturates, Thiopental, Pentobarbital, Phenobarbital, Methohexital, Benzodiazepines, Midazolam, Diazepam, Lorazepam, Dexmedetomidine, Ketamine, Sevoflurane, Isoflurane, Desflurane, Remifenanil, Fentanyl, Sufentanil, Alfentanil, and the like. However, the present disclosure recognizes that each of these drugs, induces very different characteristics or signatures, for example, within EEG data or waveforms.

The following external stimuli are examples of external stimuli that may be used with the present disclosure or which could provoke arousal to consciousness: surgical stimuli, auditory stimuli, olfactory stimuli, somatosensory stimuli, visual stimuli, noxious stimuli, and the like. Surgical stimuli could include incision, retraction, movement of instruments such as endoscopes or laryngoscopes, for example. Noxious stimuli could be provided through a variety of modalities including pressure, electrical current, or temperature. When an auditory stimulus is used, the auditory stimulus can be presented at greater than 50 decibels peak sound pressure level, greater than 60 decibels peak sound pressure level, greater than 70 decibels peak sound pressure level, or greater than 80 decibels peak sound pressure level. When somatosensory stimuli is used, similarly, different levels of intensity and noxiousness can be employed, for example, by varying the amount of pressure, the amount of electrical current, or the temperature level administered. In addition, external stimuli from these and similar modalities could occur spontaneously within clinical environments lead a patient or subject to be aroused to consciousness from an anesthesia-induced unconscious state.

With the proper drug or drugs and/or patient profile and/or external stimulus selected, acquisition of physiological data begins at process block 504, where the acquired data is EEG data. The present disclosure provides systems and methods for analyzing acquired physiological information from a patient, analyzing the information and the key indicators included therein, and extrapolating information regarding a current and/or predicted future state of the patient. To do so, rather than evaluate physiological data in the abstract, the physiological data is processed. Processing can be done in the electrode or sensor space or extrapolated to the locations in the brain. As will be described, the present disclosure enables the tracking of the spatiotemporal dynamics of the brain by combining additional analysis tools, including, for example, spectrogram, phase-amplitude modulation, coherence analyses, and so forth. As will be apparent, reference to "spectrogram" may refer to a visual representation of frequency domain information.

At process block 506, Laplacian referencing can be performed to estimate radial current densities perpendicular to the scalp at each electrode site of, for example, the monitoring device of FIG. 3A. This may be achieved by taking a difference between voltages recorded at an electrode site and an average of the voltage recorded at the electrode sites in a local neighborhood. Other combinations of information across the plurality of electrodes may also be used to enhance estimation of relevant brain states. In this manner, generated signals may be directly related to electrodes placed on a subject at particular sites, such as frontal, temporal, parietal locations, and so forth, or may be the result of combinations of signals obtained from multiple sites.

Next, at process blocks 508, 510, 512, different analyses may be performed either independently, or in any combination, to yield any of spectral, temporal, coherence, synchrony, amplitude, or phase information, related to different spatiotemporal activities at different states of a patient receiving anesthesia. In some aspects, information related to brain coherence and oscillation size may be determined in relation to slow or low-frequency oscillations and/or thalamocortical oscillations.

At process block 508, a spectral analysis may performed to yield information related to the time variation of spectral power for signals assembled from physiological data acquired at process block 504. Such spectral analysis may facilitate identification and quantification of EEG signal profiles in a target range of frequencies. In some aspects, spectrograms may be generated and processed at process block 508, for example, using multitaper and sliding window methods to achieve precise and specific time-frequency resolution and efficiency, which are properties that can be used to estimate relevant brain states. In other aspects, state-space models of dynamic spectra may be applied to determine the spectrograms, whereby the data drives the optimal amount of smoothing. Although spectrogram generation and processing may be performed at process block 508, a visual representation of the spectrograms need not be displayed.

At process block 510, a coherence analysis may be performed to give indications related to spatial coherence across local and global brain regions, using signals generated from raw or processed physiological data, as described. In particular, coherence quantifies the degree of correlation between any pair signals at a given frequency, and is equivalent to a correlation coefficient indexed by frequency. For example, a coherence of 1 indicates that two signals are perfectly correlated at that frequency, while a coherence of 0 indicates that the two signals are uncorrelated at that frequency. In some aspects, coherence may determined for signals described by specific frequency bands, such as low or slow oscillation frequencies (for example, 0.1-1 Hz), or δ (1-4 Hz), α (8-14 Hz), β (14-30 Hz), or γ (30-80 Hz) frequency bands and so forth, identified by way of a spectral analysis, as performed at process block 508. For example, a strong coherence in the a range indicates highly coordinated activity in the frontal electrode sites.

Other features of generated signals, as described, may likewise be tracked, such as phase-amplitude and phase-phase modulations. Thus, at process block 512, a phase analysis may be performed that considers the amplitude or phase of a given signal with respect to the amplitude or phase of other signals. In particular, as explained above, spectral analysis of EEG signals allows the present disclosure to track systematic changes in the power in specific frequency bands associated with administration of anesthesia, including changes in slow or low frequencies (0.1-1 Hz), δ (1-4 Hz), θ (5-8 Hz), α (8-14 Hz), β (12-30 Hz), and γ (30-80 Hz). However, spectral analysis treats oscillations within each frequency band independently, ignoring correlations in either phase or amplitude between rhythms at different frequencies. In some aspects, computations related to the extent that slow or low-frequency oscillation phases modulate the amplitudes of oscillations in other frequency bands, or spiking activity may be performed. In other aspects, phase relationships between signals, such as slow-oscillation signals, from different cortical regions may also be determined to provide synchrony information in relation to different states of a patient receiving anesthesia.

The above-described selection of an appropriate analysis context based on a selected drug or drugs (process block 502), the acquisition of data (process block 504), and the analysis of the acquired data (process blocks 508-512) set the stage for the new and substantially improved real-time analysis and reporting on the likelihood of arousing the patient to consciousness by applying an external stimulus. That is, although, as explained above, particular indications or signatures related to the states of effectiveness of an administered anesthetic compound or anesthetic compounds can be determined from each of the above-described analyses (particularly, when adjusted for a particular selected drug or drugs), the present disclosure provides a mechanism for considering each of these separate pieces of data and more to accurately indicate and/or report on the likelihood of arousing the patient to consciousness by applying an external stimulus.

Specifically, referring to process block 514, any and all of the above-described analysis and/or results can be combined and reported, in any desired or required shape or form, including providing a report in real time, and, in addition, can be coupled with a precise statistical characterizations of behavioral dynamics, for use by a clinician or use in combination with a closed-loop system as described above. In some aspects, information related to EEG frequency and amplitude may be employed. In particular, behavioral dynamics, such as the likelihood of arousing a patient to consciousness can be precisely and statistically calculated and indicated in accordance with the present disclosure. To do so, the present disclosure may use dynamic Bayesian methods that allow accurate alignment of the spectral, coherence and phase analyses relative to behavioral markers.

Figure 5B:
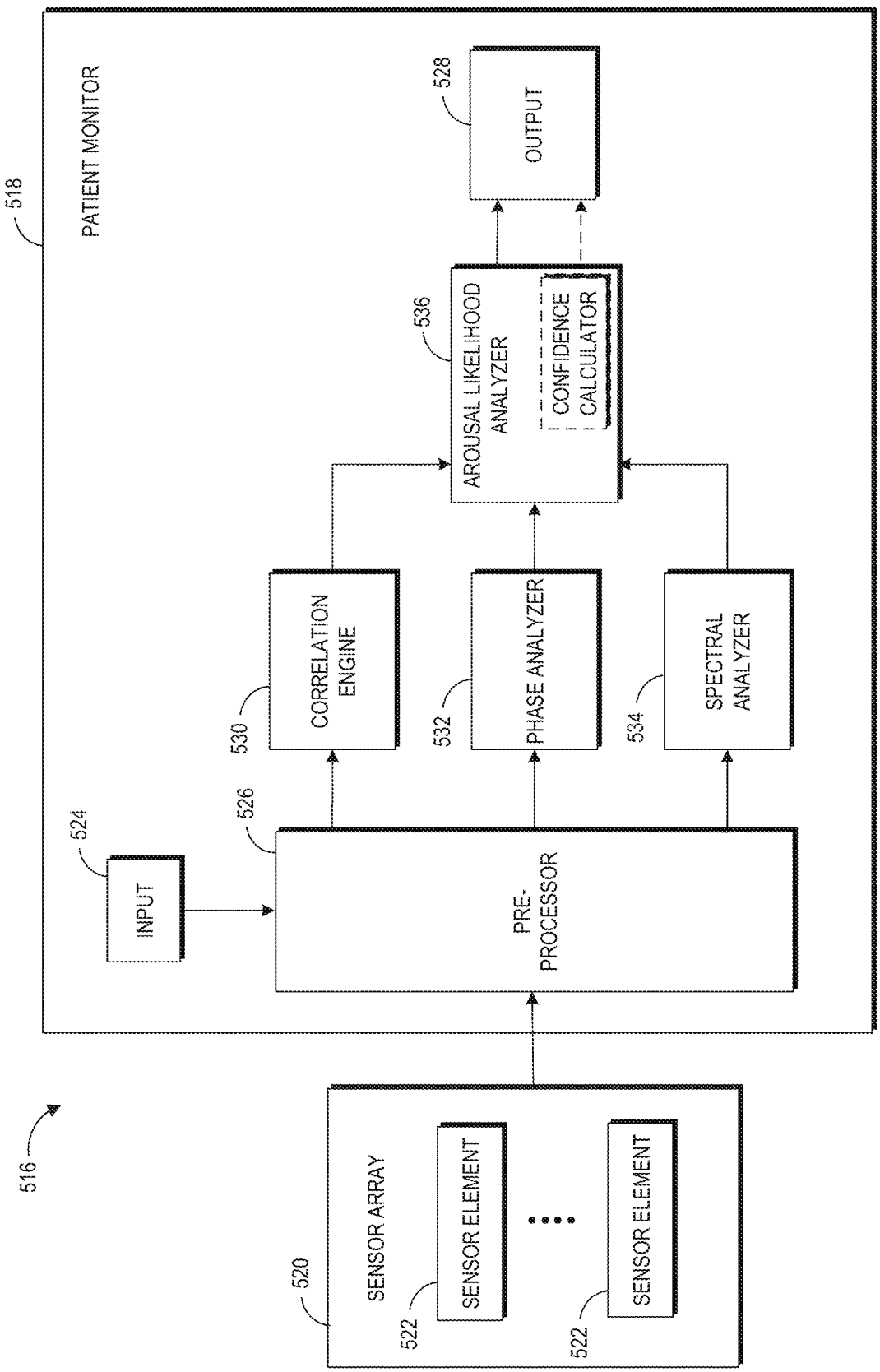
FIG. 5B is an example system for use in determining a brain state of a patient, in accordance with the present disclosure.

Referring to FIG. 5B, a system 516 for carrying out steps for determining a brain state of a patient, as described above, is illustrated. The system 516 includes patient monitor 518 and a sensor array 520 configured with any number of sensors 522 designed to acquire physiological data, such as EEG data. The sensor array 520 is in communication with the patient monitor 518 via a wired or wireless connection.

The patient monitor 518 can be configured to receive and process data provided by the sensor array 522, and can include an input 524, a pre-processor 526 and an output 528. In particular, the pre-processor 526 can be configured to carry out any number of pre-processing steps, such as assembling the received physiological data into time-series signals and performing a noise rejection step to filter any interfering signals associated with the acquired physiological data. The pre-processor can also be configured to receive an indication via the input 524, such as information related to administration of an anesthesia compound or compounds, and/or an indication related to a particular patient profile, such as a patient's age, height, weight, gender, or the like, as well as drug administration information, such as timing, dose, rate, and the like, and/or information regarding the external stimulus intended to be used to arouse the patient. The patient monitor 518 further includes a number of processing modules in communication with the pre-processor 526, including a correlation engine 530, a phase analyzer 532 and a spectral analyzer 534. The processing modules are configured to receive pre-processed data from the pre-processor 526 and carry out steps necessary for determining a brain state of a patient, as described, which may be performed in parallel, in succession or in combination. Furthermore, the patient monitor 518 includes an arousal likelihood analyzer 536 which is configured to received processed information, such as frequency and amplitude information, from the processing modules and provide a determination related to a likelihood of arousing a patient using an external stimulus and confidence with respect to the determined likelihood. Information related to the likelihood may then be relayed to the output 528, along with any other desired information, in any shape or form. For example, the output 528 may include a display configured to provide a likelihood indicator and confidence indicator, either intermittently or in real time.

Figure 6:
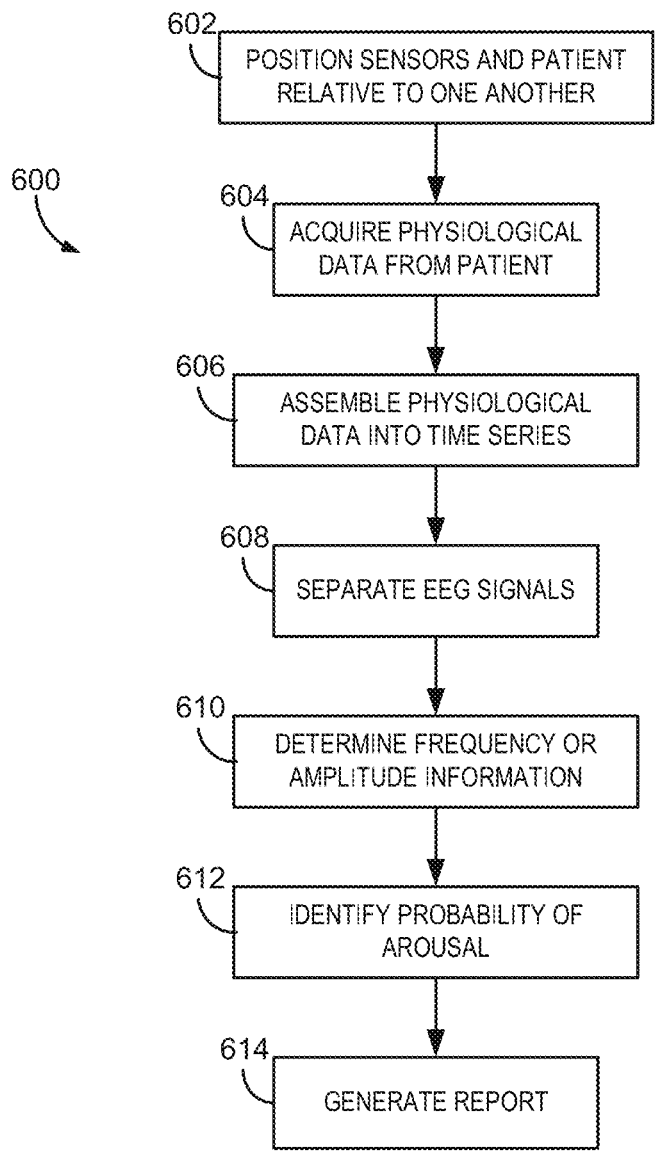
FIG. 6 is a flow chart setting forth steps of a method for monitoring a patient in accordance with the present disclosure.

Turning now to FIG. 6, a flow chart is illustrated setting forth steps of a method for monitoring a patient in accordance with the present disclosure. The process 600 begins at process block 602, whereby any number of sensors may be arranged on a subject, and a clinician or operator may provide at least one indication related to the administration of a drug, a patient characteristic, or the kind and/or quality of an external stimulus that is intended to be applied to the patient. It should be appreciated that rather than arranging sensors on the subject, the sensors and patient can be positioned relative to one another, or the patient can be positioned relative to the sensors (i.e., the sensors can be stationary and the patient can be positioned in relation to the stationary sensors). Then, at process block 604, any amount of physiological data may be acquired, which may then, at process block 606, be arranged into time-series data. Subsequently, at process block 608, EEG signals may be separated from the time-series data, using any approach for isolating EEG signals. Such signals may, in some aspects, be representative of a frequency range as described herein, such as the slow frequency range, or of a location, such as the thalamocortical region. Using at least indicators from such EEG signals, at least one of a frequency or amplitude information may be generated. Such information may provide spatiotemporal signatures, as described, which, when employed in association with a model, may identify brain states at process block 612, including at least one of a likelihood or probability of arousing the patient to consciousness by applying an external stimulus. Finally, at process block 614, a report may be generated, taking any shape or form, as desired or required. Such report may provide an indication to a clinician regarding the probability of arousing the patient to consciousness by applying an external stimulus.

The above-described systems and methods may be further understood by way of examples. These examples are offered for illustrative purposes only, and are not intended to limit the scope of the present disclosure in any way. Indeed, various modifications of the disclosure in addition to those shown and described herein will become apparent to those skilled in the art from the foregoing description and the following examples and fall within the scope of the appended claims. For example, specific examples of brain states, medical conditions, levels of anesthesia or sedation and so on, in association with specific drugs and medical procedures are provided, although it will be appreciated that other drugs, doses, states, conditions and procedures, may be considered within the scope of the present disclosure. Furthermore, examples are given with respect to specific indicators related to brain states, although it may be understood that other indicators and combinations thereof may also be considered within the scope of the present disclosure. Likewise, specific process parameters are recited that may be altered or varied based on variables such as signal amplitude, phase, frequency, duration and so forth.

Example I

Although some EEG patterns are observed consistently during certain procedures, it is unclear how they are functionally related to unconsciousness. Specifically, other anesthetic drugs, such as ketamine and dexmedetomidine, operate through molecular and neural circuit mechanisms that may be different from those of propofol. For example, similar EEG patterns are known to arise for different drugs, such as with propofol, an γ-Aminobutyric acid receptor-specific agonist ($GABA_A$), and dexmedetomidine, an α2-adrenoceptor agonist. Propofol is associated with well-coordinated frontal thalamocortical alpha oscillations and asynchronous slow oscillations. Similarly, dexmedetomidine gives rise to spindle-like activity detected in the 8-12 Hz range over the frontal region and slow oscillations. As such, although EEG patterns observed during administration appear superficially similar, different behavioral or clinical properties may be exhibited. For example, unlike patients receiving propofol, patients receiving an infusion of dexmedetomidine can be easily aroused with gentle verbal or tactile stimuli at blood concentration levels required to maintain loss of consciousness (LOC). This leads to the natural question of whether there are differences in the brain dynamics induced by different drugs that can explain the observed differences in clinical response and behavior, and whether such brain dynamics can be detected in the EEG.

To investigate shared relationships between the EEG activity of dexmedetomidine and propofol, and altered states of arousal, intraoperative frontal EEG were recorded from patients undergoing light sedation with dexmedetomidine, sedation with propofol and general anesthesia (GA) with propofol. As described below, EEG dynamics, using time-varying spectral, and coherence methods revealed that, although the mean group level spectrograms appeared qualitatively similar, the patterns of coherence in the 0.1-1 Hz and 8-12 Hz EEG frequency bands were different. Dexmedetomidine induces 0.1-1 Hz slow oscillations that exhibited greater coherence compared to propofol slow oscillations. This finding is consistent with the observation that sleep-related slow oscillations are highly synchronous, while propofol-induced slow oscillations are asynchronous and reflect a state of fragmented cortical communication. Conversely, dexmedetomidine induced 8-12 Hz oscillations exhibited less coherence than propofol induced oscillations. This is consistent with the notion that coherence of 8-12 Hz oscillations represents an entrainment of frontal thalamo-cortical circuits that block communication. Notably, these differences in coherence vary appropriately with the levels of consciousness represented by the three groups studied.

In addition, to study the relationship between EEG dynamics in context of potential neural circuit mechanisms of an anesthetic vapor, intra-operative EEG were recorded from patients undergoing general anesthesia with sevoflurane as the primary maintenance agent, which is an ether derivative commonly used to maintain GA. Unlike the intravenous anesthetic agent propofol, the EEG signature of sevoflurane, has not been well studied. Connectivity analysis was then performed on the EEG dynamics postulated to be involved in anesthesia-induce depression in consciousness. As described below, it was found that during GA induced unconsciousness the macroscopic EEG dynamics of sevoflurane closely resemble those of propofol. These observed similarities are consistent with present understanding of how EEG features relate to anesthesia-induced depression of consciousness, and provide a framework for further experimental studies on the neural circuit mechanisms of general anesthesia.

Methods

Patient Selection and Data Collection

A 64-channel electroencephalogram was measured under dexmedetomidine (n=9) and propofol (n=8) in healthy volunteers, 18-36 years of age. These studies were approved by the Human Research Committee at the Massachusetts General Hospital. All subjects provided informed consent and were American Society of Anesthesiology Physical Status I with Mallampati Class I airway anatomy. In addition to standard pre-anesthesia assessments, a urine toxicology screen was performed to ensure that subjects had not taken drugs that might confound the electroencephalogram or behavioral results. We administered a urine pregnancy test for each female subject to confirm that they were not pregnant. Before the start of the study, we required subjects to take nothing by mouth for at least 8 hours. For dexmedetomidine-induced unconsciousness, a 1 mcg/kg loading bolus over 10 minutes, followed by a 0.7 mcg/kg/hr infusion (×50 minutes) was administered. For propofol-induced unconsciousness, we used a computer-controlled infusion to achieve propofol target effect-site concentrations of 0, 1, 2, 3, 4, and 5 µg/mL. We maintained each target effect-site concentration level for 14 min. During the study, subjects breathed 21% oxygen by volume (dexmedetomidine), and 30% oxygen by volume (propofol). When a subject became apneic, an anesthesiologist assisted breathing with bag/mask ventilation (propofol). Each subject's heart rate was monitored with an electrocardiogram, oxygen saturation through pulse oximetry, respiration and expired carbon dioxide with capnography, and blood pressure cuff (dexmedetomidine) or arterial line (propofol). During induction and emergence from dexmedetomidine- and propofol-induced unconsciousness, electroencephalograms were recorded using a 64-channel BrainVision Magnetic Resonance Imaging Plus system (Brain Products, Munich, Germany) with a sampling rate of 1,000 Hz (dexmedetomidine) and 5000 Hz (propofol), resolution 0.5 µV least significant bit, bandwidth 0.016-1000 Hz.

Volunteers were instructed to close their eyes throughout the study to avoid eye-blink artifacts in the electroencephalogram. Volunteers were presented with auditory stimuli during the study and asked to respond by button presses to assess the level of conscious behavior. For dexmedetomidine, the stimuli consisted of the volunteer's name presented every two minutes. For propofol, the stimuli consisted of either a verbal stimulus or an auditory click, which were presented every 4 s in a repeating sequence of click-click-verbal-click-click, with a total of 210 stimuli per target effect-site concentration level. Verbal stimuli consisted either of the subject's name or a word randomized with an equal number of name or word stimuli at each level. The click train was delivered binaurally, with 40-Hz clicks in the left ear and 84-Hz clicks in the right ear. Subjects were instructed to press one button if they heard their name and to press the other button if they heard any other stimulus. Stimuli were recorded at a sampling rate of 44.1 kHz and were presented using Presentation software (Neurobehavioral Systems, Inc., Berkeley, Calif.) with ear-insert headphones (ER2; Etymotic Research, Elk Grove Village, Ill.) at ~81 decibels peak sound pressure level. Button-press stimuli were recorded using a custom-built computer mouse with straps fitted to hold the first and second fingers in place over the mouse buttons. The mouse was also lightly strapped to the subject's hand using tape and an arterial line board to ensure that responses could be recorded accurately. Details for study procedures, and data collection for the propofol data can be found in Purdon et al., Proc Natl Acad Sci USA 2013; 110: E1142-51 and Cimenser et al., Proc Natl Acad Sci USA 2011; 108: 8832-7, the entire contents of which are incorporated herein by reference.

Behavioral Analysis

The likelihood of response to the verbal stimuli under propofol was estimated using Bayesian Monte Carlo methods to fit a state-space model to the data.

EEG Preprocessing and Epoch Selection

An anti-aliasing filter was applied and the EEG data was downsampled to 250 Hz before analysis. EEG signals were re-montaged to a nearest-neighbor Laplacian reference, using distances along the scalp surface to weigh neighboring electrode contributions.

First, 2-minute EEG segments were selected from all subjects during the awake, eyes closed baseline. Eye closure facilitates distinguishing between normal awake, eyes-closed occipital alpha oscillations and the frontal alpha oscillations associated with anesthesia induced altered arousal.

Electroencephalogram data segments were selected based on the behavioral response. For dexmedetomidine, the onset of unconsciousness was defined as the first failed behavioral response that was followed by a series of at least five successive failures (10-minutes). To characterize the electroencephalogram signature of dexmedetomidine-induced unconsciousness, we used the first 2-minute electroencephalogram epoch obtained for each volunteer 8-minutes after the onset unconsciousness.

For propofol, data segments were identified using a combination of behavioral and neurophysiological endpoints. Two states were identified, one where subjects had a non-zero probability of response to auditory stimuli, and another where subjects were unconscious with a zero probability of response, propofol-induced unconsciousness trough-max (TM) and propofol-induced unconsciousness peak-max (PM) respectively. Eight volunteers exhibited the propofol-induced unconsciousness (TM) and propofol-induced unconsciousness (PM) electroencephalogram states. In the trough-max pattern, propofol-induced alpha waves are strongest at the troughs of the slow oscillation. This pattern begins ~20 min before loss of consciousness and extends ~10 min after loss of consciousness (the troughs are Laplacian surface-negative deflections). This pattern arises during the transitions to and from unconsciousness, and bisects unconsciousness defined by loss of response to auditory stimuli. As such, the TM pattern marks the earliest part of propofol-induced alterations in consciousness that was neurophysiologically identified to border the states of consciousness and unconsciousness. For each volunteer subject, TM electroencephalogram epochs were chosen that occurred within the first 2-minutes of the onset of this pattern. In the PM pattern, propofol-induced alpha waves are strongest at the peaks of the slow oscillation. That is, the phase-amplitude modulation shifted by 180°, such that the alpha amplitudes were largest at the peaks of low-frequency oscillations (the peaks are Laplacian surface-positive deflections). PM coupling is a propofol-induced signature of unconsciousness in the cortex that precedes the onset of burst suppression. Importantly, this pattern arises after loss of consciousness, when the probability of response to auditory stimuli is zero. Clinically, this neurophysiological pattern can be related to a general anesthetic state. For each volunteer subject, PM electroencephalogram epochs were chosen that occurred within the first 2-minutes of the onset of this pattern. These neurophysiological signatures are stably maintained over changing propofol effect site concentrations; ~1-2 μg/mL for trough max and ~3-5 μg/mL for PM. As used herein, this disclosure refers to the selected TM electroencephalogram epoch as "propofol-induced unconsciousness (TM)," and the selected PM electroencephalogram epoch as "propofol-induced unconsciousness (PM)." Table 1 provides a clinical context to the behavioral states from which these electroencephalogram epochs were obtained.

Spectral Analysis

Figure 7A:
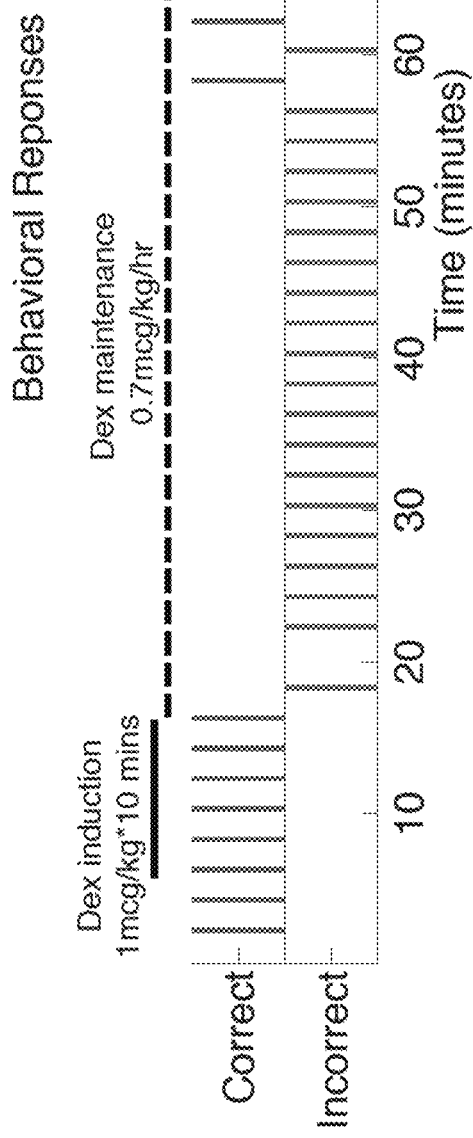
FIG. 7A is a representative behavioral response, as described in Example 1.
Figure 7B:
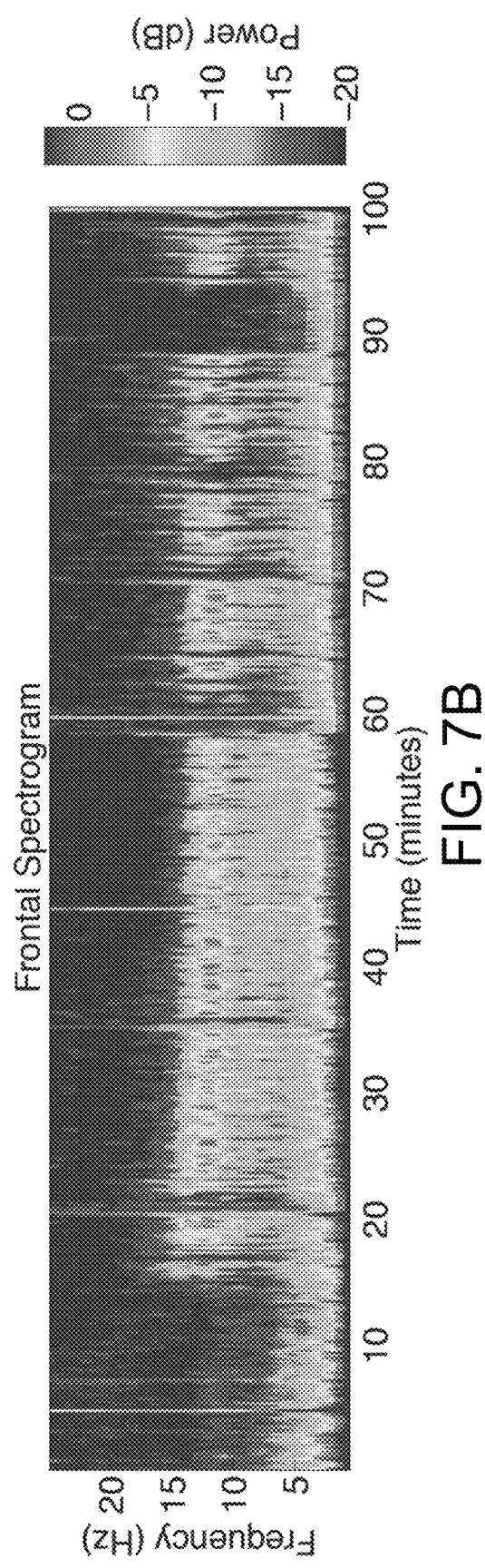
FIG. 7B is a frontal spectrogram corresponding to the behavioral response in FIG. 7A.
Figure 7C:
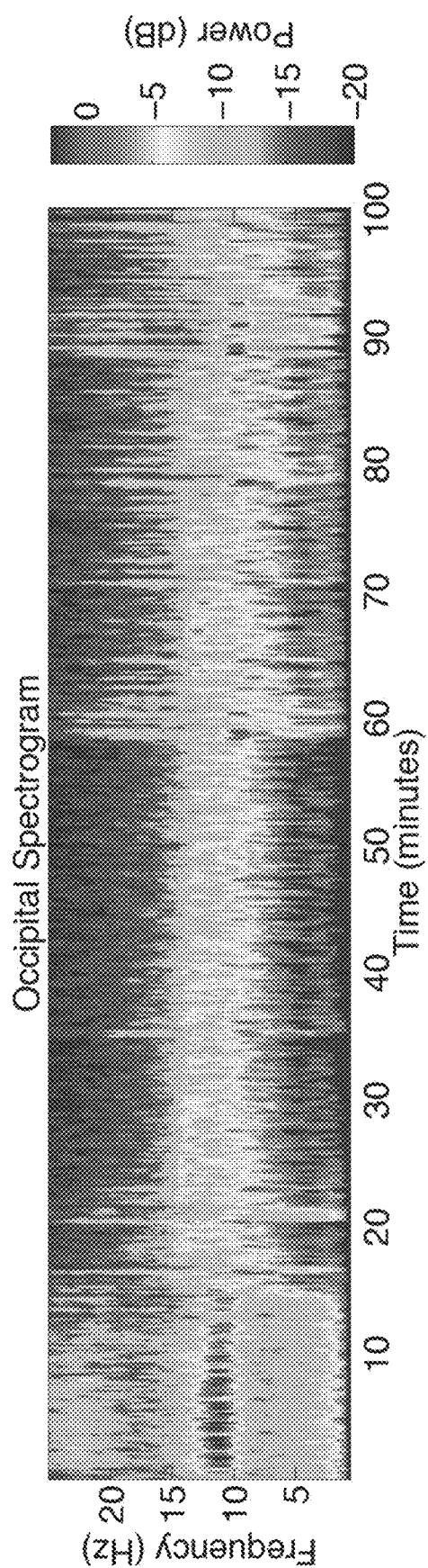
FIG. 7C is an occipital spectrogram corresponding to the behavioral response in FIG. 7A.

The power spectral density, also referred to as the power spectrum or spectrum, quantifies the frequency distribution of energy or power within a signal. The spectrogram is a time-varying version of the spectrum. For example, FIGS. 7A, 7B, and 7C show the behavioral response and representative frontal and occipital volunteer electroencephalogram spectrograms under dexmedetomidine. Also, FIG. 8A shows representative frontal spectrograms of dexmedetomidine-induced unconsciousness, propofol-induced unconsciousness (TM) and propofol-induced unconsciousness (PM). In these spectrograms, frequencies are arranged along the y-axis, and time along the x-axis, and power is indicated by color on a decibel (dB) scale. FIG. 8B shows representative raw electroencephalogram signals in the time domain, and 8-16 Hz and 0.1-1 Hz bandpass filtered electroencephalogram signals in the time domain. Spectra and spectrograms were computed using the multitaper method, implemented in the Chronux toolbox.

TABLE 1

Behavioral Characteristics of Selected Electroencephalogram Epochs

| Selected Electroencephalogram Epochs | Probability of Response to Verbal Stimuli (%) mean (±SD) | Behavioral State |
|---|---|---|
| Dexmedetomidine-induced unconsciousness | Not Measured | Sedation |
| Propofol-induced unconsciousness (TM) | 91.5 (15.4) | Sedation |

TABLE 1-continued

Behavioral Characteristics of Selected Electroencephalogram Epochs

| Selected Electroencephalogram Epochs | Probability of Response to Verbal Stimuli (%) mean (±SD) | Behavioral State |
|---|---|---|
| Propofol-induced unconsciousness (PM) | 0 | General Anesthesia |

In general, anesthesia-related oscillations have a bandwidth of approximately 0.5 to 1 Hz for slow and alpha and spindle oscillations. Anesthesia-induced beta and gamma oscillations tend to be wider, approximately 5 Hz or more in bandwidth. The spectral analysis parameters can be chosen to make these oscillations clearly visible and distinguishable from one another, while also ensuring sufficient temporal resolution to track time-varying changes. For instance, if narrower spectral resolution were required, a longer window length T could be chosen, but with the tradeoff that rapid time-varying changes would be more difficult to discern. Similarly, the time-bandwidth product TW could be reduced to improve spectral resolution, but with the tradeoff that fewer tapers could be used (K<=2TW−1), resulting in increased variance. Similarly, a shorter window length T could be chosen to improve temporal tracking, and a wider time-bandwidth product TW could be chosen to improve variance, both with the tradeoff of lower spectral resolution. In general, these spectral analysis parameters can be varied from the example provided here in order to enhance or optimize detection, visualization, and temporal tracking of the anesthetic or sedative properties of interest. Moreover, different sets of parameters could be used or made available for different drugs or clinical scenarios.

Group-level spectrograms were computed by taking the median across volunteers. Spectra were also calculated for selected EEG epochs. The resulting spectra were then averaged for all epochs, and 95% confidence intervals were computed via taper-based jackknife techniques. The spectral analysis parameters included window length T=4 s with 0s overlap, time-bandwidth product TW=3, number of tapers K=5, and spectral resolution 2 W of 1.5 Hz. Peak power, and its frequency, was estimated for the dex-spindle, travelling peak, and frontal alpha oscillations for each individual subject. Averages across subjects were performed to obtain the group-level peak power and frequency for these oscillations.

Coherence Analysis

Figure 14:
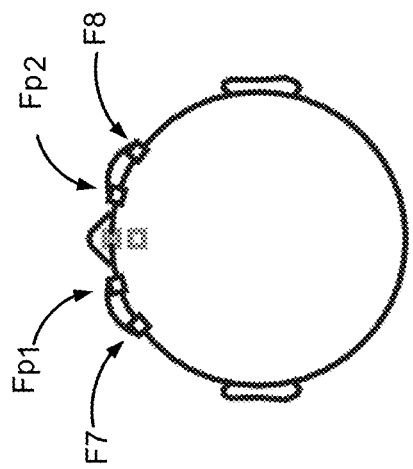
FIG. 14 is a schematic showing placement of various sensors on a patient's head, as described in Example 1.

The coherence quantifies the degree of correlation between two signals at a given frequency. It is equivalent to a correlation coefficient indexed by frequency: a coherence of 1 indicates that two signals are perfectly correlated at that frequency, while a coherence of 0 indicates that the two signals are uncorrelated at that frequency. The coherence $C_{xy}(f)$ function between two signals x and y is defined as:

$$C_{xy}(f) = \frac{|S_{xy}(f)|}{\sqrt{S_{xx}(f)S_{yy}(f)}}$$

where $S_{xy}(f)$ is the cross-spectrum between the signals x(t) and y(t), $S_{xx}(f)$ is the power spectrum of the signal x(t) and $S_{yy}(f)$ is the power spectrum of the signal y(t). Similar to the spectrum and spectrogram, the coherence can be estimated as a time-varying quantity called the coherogram. Coherograms were computed between two frontal EEG electrodes, namely F7 and F8 (FIG. 14), using the multitaper method, implemented in the Chronux toolbox (http://chronux.org). The multitaper method was chosen specifically because it allows the spectral resolution to be set precisely, which is required to observe many anesthesia-related phenomena. Moreover, for a particular choice of spectral resolution, the multitaper method offers lower bias and lower variance than traditional nonparametric spectral estimation methods. Such lower bias and variance results in displays that are visually clearer, with oscillations or peaks that are more distinct, and facilitates greater sensitivity and specificity in subsequent processing or inference steps. Group-level coherograms were computed by taking the median across volunteers. Coherence was also calculated for the selected EEG epochs. The resulting coherence estimates were then averaged for all epochs, and 95% confidence intervals were computed via taper-based jackknife techniques. The coherence analysis parameters were: window length T=4 s with 0s overlap, time-bandwidth product TW=3, number of tapers K=5, and spectral resolution 2 W of 1.5 Hz. Peak coherence, and its frequency, was estimated for the dex-spindle, travelling peak, and frontal alpha oscillation for each individual subject. Averages across subjects were performed to obtain group-level peak coherence and frequency for these oscillations. The coherence provides information equivalent to the magnitude of the PLF, as described. Thus, the changes in low-frequency coherence described below reflect the same changes in cortical dynamics described above in terms of the PLF.

Statistical Analysis

To compare spectral and coherence estimates between groups, jackknife-based methods were used, namely the two-group test for spectra (TGTS), and the two-group test for coherence (TGTC), as implemented by the Chronux toolbox (http://www.chronux.org). This method accounts for the underlying spectral resolution of the spectral and coherence estimates, and considers differences to be significant if they are present for contiguous frequencies over a range greater than the spectral resolution 2 W. Specifically, for frequencies f>2 W, the null hypothesis was rejected only if the test statistic exceeded the significance threshold over a contiguous frequency range ≥2 W. For frequencies 0≤f≤2 W, to account for the properties of multitaper spectral estimates at frequencies close to zero, the null hypothesis was rejected only if the test statistic exceeded the significance threshold over a contiguous frequency range from 0 to max(f,W)≤2 W. A significance threshold of p<0.05 was selected for within group comparisons and p<0.001 for between group comparisons, applying a Bonferonni correction for multiple comparisons where appropriate.

Results

Dexmedetomidine Vs. Baseline Power Spectra

Figures 9C, 10A:
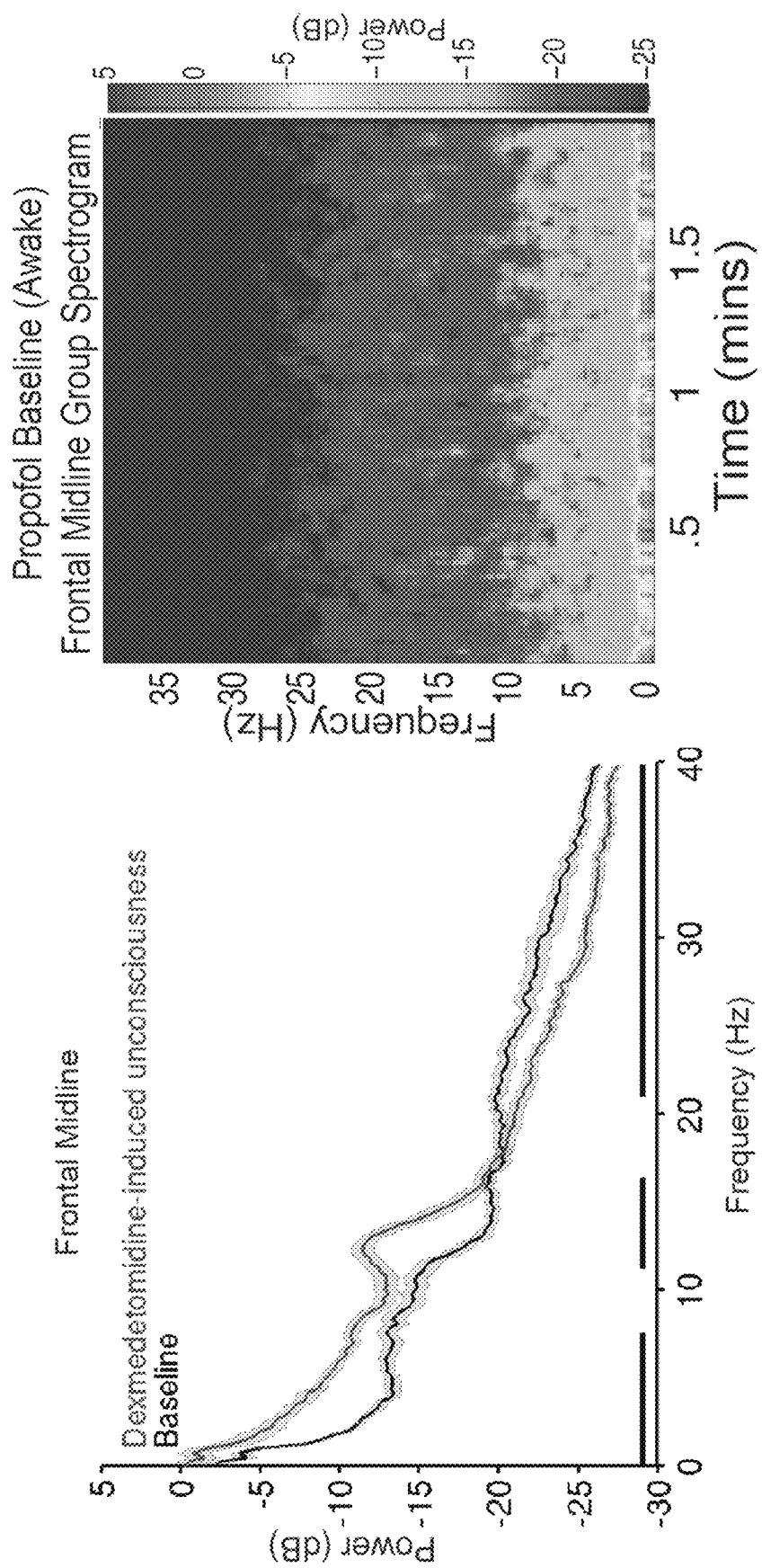
FIG. 9C is the power spectra of dexmedetomidine baseline vs. dexmedetomidine-induced unconsciousness, as described in Example 1.
FIG. 10A is a group level spectrogram of propofol baseline, as described in Example 1.

Differences were observed in the spectrogram that were induced by dexmedetomidine. Compared to baseline, the spectrogram during dexmedetomidine-induced unconsciousness exhibited increased power across a frequency range of 2-15 Hz (FIGS. 9A and 9B). The EEG spectrum was then compared during dexmedetomidine-induced unconsciousness to baseline, and significant differences were found in power across most frequencies between 0 and 40 Hz. EEG power exhibited a dex-spindle oscillation peak (mean±std; peak frequency, 12.9 Hz±0.7; peak power, ~10.8 dB±0.3.6), and was larger during dexmedetomidine-induced unconsciousness across a range of frequencies less than 16.6 Hz (FIG. 9C; 0.1-7.8 Hz, 11.5-16.6 Hz; P<0.001, TGTS). EEG power was lower during dexmedetomidine-induced unconsciousness in beta/gamma frequency ranges (FIG. 9C; 21.2-40 Hz; P<0.001, TGTS). In FIG. 9C, the median spectra represented with 95% jackknife confidence intervals are shown. Horizontal black lines represent frequency ranges at which significant differences existed. These results show that, compared to the awake-state, slow/delta and spindle oscillations (dex-spindles) are exhibited during dexmedetomidine-induced unconsciousness.

Propofol Vs. Baseline Power Spectra

Figures 10B, 10C:
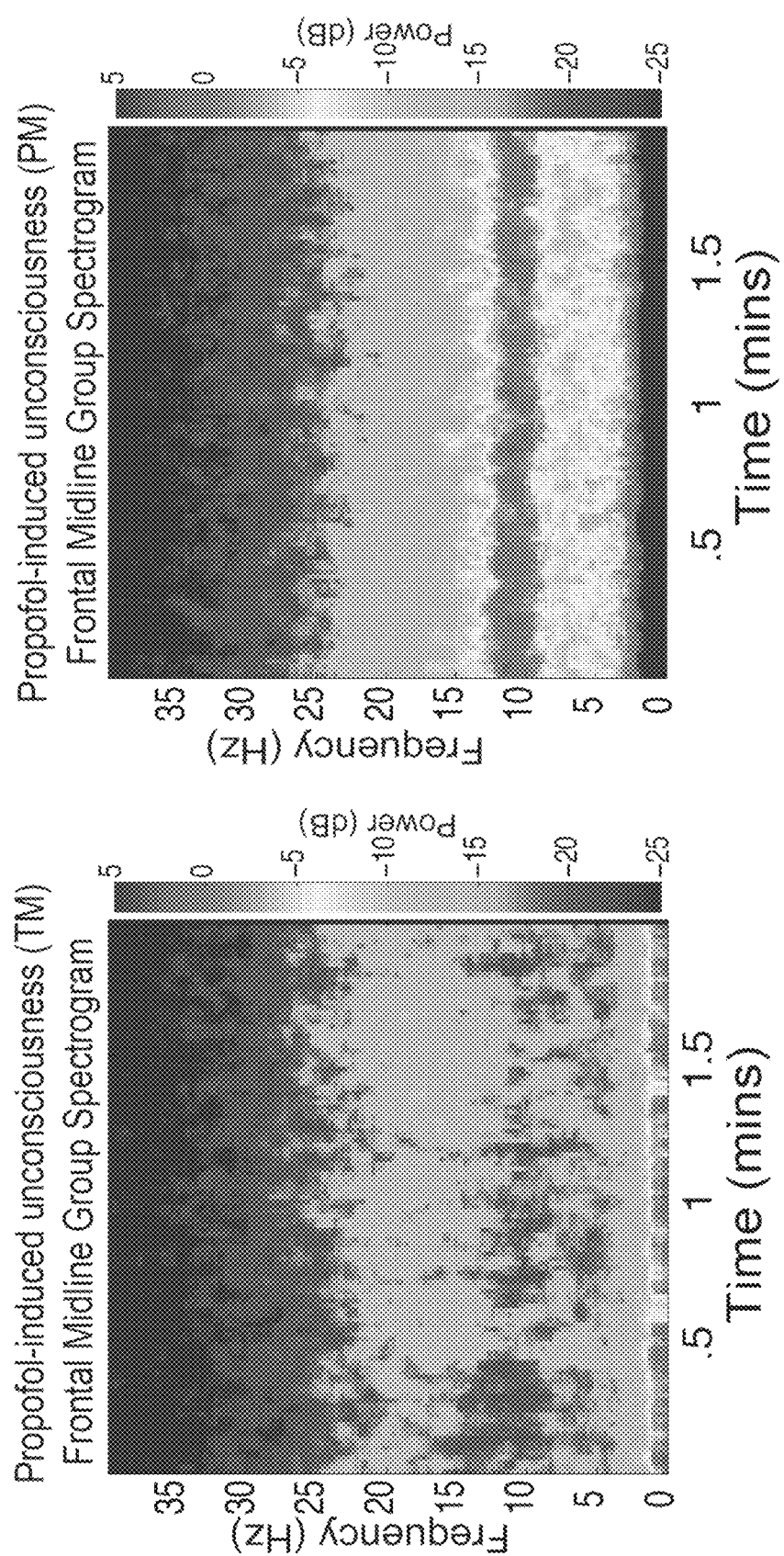
FIG. 10B is a group level spectrogram of propofol-induced unconsciousness (TM), as described in Example 1.
FIG. 10C is a group level spectrogram of propofol-induced unconsciousness (PM), as described in Example 1.

Differences were observed in the spectrogram that were induced by propofol. Propofol-induced unconsciousness (TM) was characterized by broad-band (~1-25 Hz) increased power whereas during propofol-induced unconsciousness (PM), the increased power appeared confined to slow, delta and alpha frequency bands (FIGS. 10A, 10B, and 10C). The EEG spectrum was then compared during propofol-induced unconsciousness (TM) and propofol-induced unconsciousness (PM) to the baseline EEG and to each other. During propofol-induced unconsciousness (TM), EEG power was significantly larger than baseline across a broad frequency range spanning alpha, beta and gamma frequencies (FIG. 10D, 10.5 Hz-50 Hz; P<0.0003, TGTS).

Figures 10D, 10E:
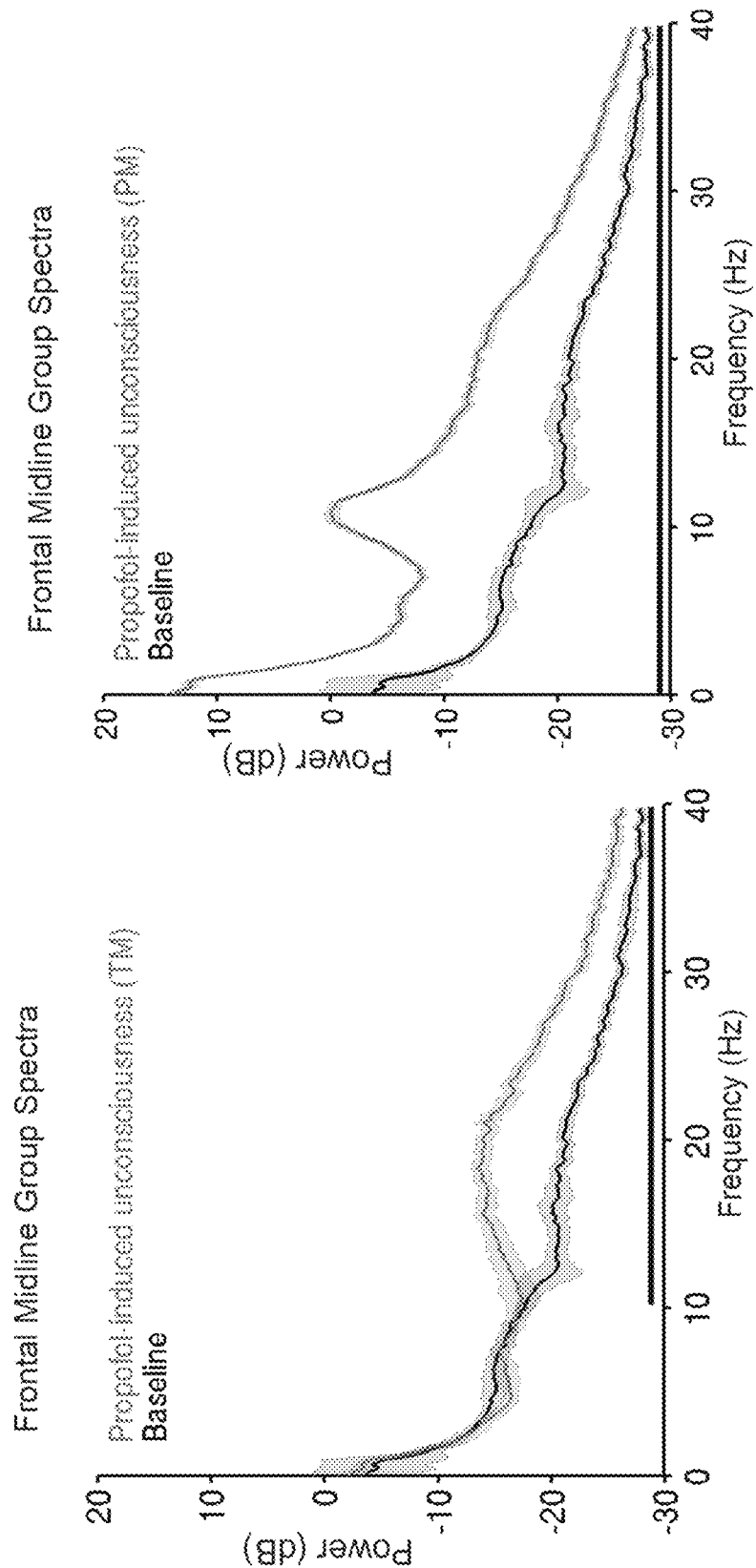
FIG. 10D is the power spectra of propofol baseline vs. propofol-induced unconsciousness (TM), as described in Example 1.
FIG. 10E is the power spectra of propofol baseline vs. propofol-induced unconsciousness (PM), as described in Example 1.

During propofol-induced unconsciousness (PM), EEG power exhibited an alpha oscillation peak (peak frequency, 10.8 Hz±0.7; peak power, 1.1 dB±4.5) and was significantly larger than baseline across all frequencies studied (FIG. 10E; 0.1-40 Hz; P<0.0003, TGTS).

Figures 10F, 11A:
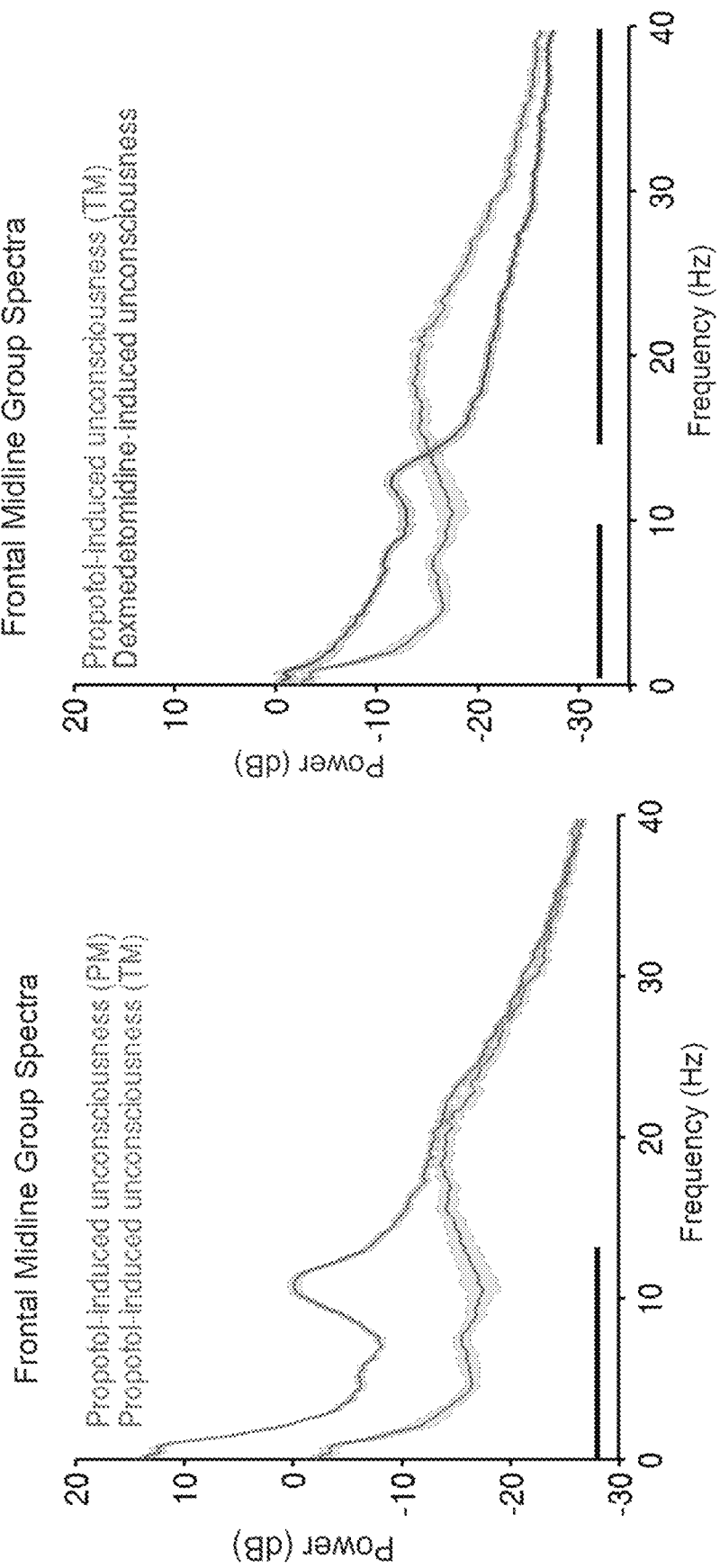
FIG. 10F is the power spectra of propofol-induced unconsciousness (TM) vs. propofol-induced unconsciousness (PM), as described in Example 1.
FIG. 11A is the power spectra of dexmedetomidine-induced unconsciousness vs. propofol-induced unconsciousness (TM), as described in Example 1.

When the power was compared between the TM and PM propofol EEG epochs, oscillations during propofol-induced unconsciousness (PM) were significantly larger across slow, delta, theta and alpha frequencies (FIG. 10F, 0.1-13.4 Hz; P<0.0003, TGTS). Slow oscillation power during propofol-induced unconsciousness (PM) (power, 13.2 dB±2.4) was larger than during propofol-induced unconsciousness (TM) (power, −2.5 dB±3.1). This means that the amplitude of slow-oscillations during propofol-induced unconsciousness (PM) was approximately 6-fold larger than during propofol-induced unconsciousness (TM), and the baseline state.

Qualitatively, during propofol-induced unconsciousness (PM), the EEG spectrogram exhibited a visibly narrower 8-12 Hz oscillation bandwidth compared to propofol-induced unconsciousness (TM) (FIGS. 10B and 10C). These results are consistent with reports that frontal alpha oscillations are exhibited during propofol-induced unconsciousness (PM), and that higher-frequency beta-gamma oscillations are observed during propofol-induced unconsciousness (TM).

Propofol and Dexmedetomidine-Induced EEG Patterns

The EEG spectra during dexmedetomidine-induced unconsciousness were compared to the EEG spectra during propofol-induced unconsciousness (TM) and propofol-induced unconsciousness (PM). The EEG power was larger during dexmedetomidine-induced unconsciousness compared to propofol-induced unconsciousness (TM) in a frequency range spanning slow, delta, theta and alpha frequencies (Fig. {FILL}; 0.7-10 Hz; P<0.0005, TGTS). We also found that propofol-induced unconsciousness (TM) EEG power was larger in a frequency range spanning beta, and gamma frequencies (Fig. {FILL}; 14.9-40 Hz; P<0.0005, TGTS). Qualitatively, the spectrum during dexmedetomidine-induced unconsciousness showed a clear dex-spindle peak at ~13 Hz, while propofol-induced unconsciousness (TM) did not exhibit a clearly distinguishable peak. During propofol-induced unconsciousness (PM), EEG power was significantly larger than dexmedetomidine-induced unconsciousness across all frequencies between 0.1 and 40 Hz (Fig. {FILL}; 0.1-40 Hz; P<0.0005, TGTS). Slow oscillation power during propofol-induced unconsciousness (PM) (power, 13.2 dB±2.4) was larger than during dexmedetomidine-induced unconsciousness (power, −0.4 dB±3.1). This means that the amplitude of slow oscillations during propofol-induced unconsciousness (PM) was approximately 4.8-fold larger than dexmedetomidine-induced unconsciousness slow oscillations. Similarly, during propofol-induced unconsciousness (PM), the EEG exhibited frontal alpha oscillations (power, 1.1 dB±4.5), which were also larger than the dex-spindles (power, −10.8 dB±3.6). This means that the amplitude of alpha oscillations during propofol-induced unconsciousness (PM) was approximately 3.9-fold larger than dexmedetomidine-induced unconsciousness spindle oscillations. These results show that the spindle-like EEG pattern induced by dexmedetomidine is distinct from the propofol-induced frontal alpha oscillations. Also, amplitude wise, propofol-induced unconsciousness (PM) slow oscillations were much larger than dexmedetomidine-induced unconsciousness slow oscillations.

Dexmedetomidine Vs. Propofol Power Spectra

Figures 11B, 12A:
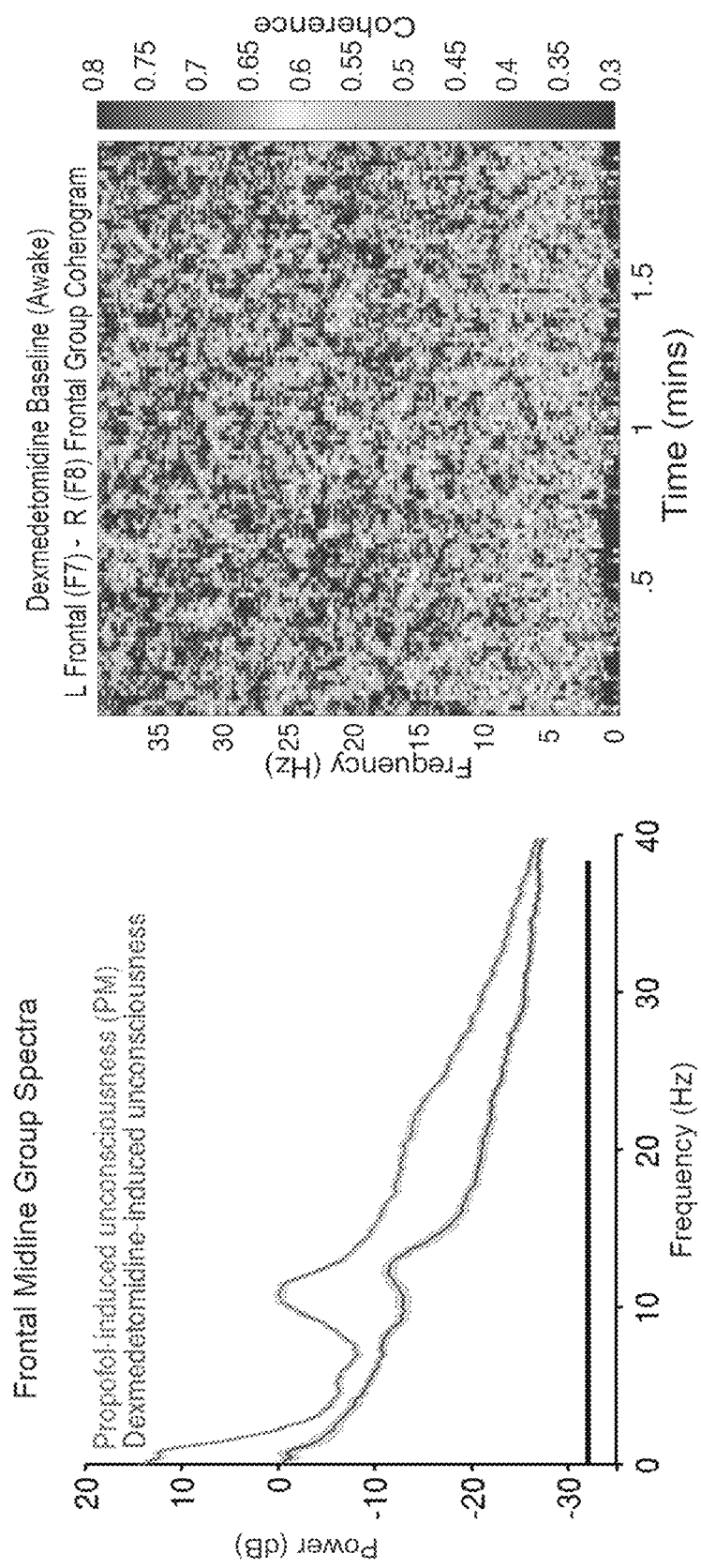
FIG. 11B is the power spectra of dexmedetomidine-induced unconsciousness vs. propofol-induced unconsciousness (PM), as described in Example 1.
FIG. 12A is a group level coherogram of dexmedetomidine baseline, as described in Example 1.

Next the spectra during dexmedetomidine-induced unconsciousness were compared to propofol-induced unconsciousness (TM) and propofol-induced unconsciousness (PM). EEG power was larger during dexmedetomidine-induced unconsciousness compared to propofol-induced unconsciousness (TM) unconsciousness in a frequency range spanning slow, delta, theta and alpha frequencies (FIG. 11A, 0.7-10 Hz; P<0.0005, TGTS). Also, propofol-induced unconsciousness (TM) EEG power was larger in a frequency range spanning beta, and gamma frequencies (FIG. 11A, 14.9-40 Hz; P<0.0005, TGTS). Qualitatively, the spectrum during dexmedetomidine-induced unconsciousness showed a clear dex-spindle peak at ~13 Hz, while propofol-induced unconsciousness (TM) did not exhibit a clearly distinguishable peak. During propofol-induced unconsciousness (PM), electroencephalogram power was significantly larger than dexmedetomidine-induced unconsciousness across all frequencies between 0.1 and 40 Hz (FIG. 11B, 0.1-40 Hz; P<0.0005, TGTS). Slow oscillation power during propofol-induced unconsciousness (PM) (power, 13.2 dB±2.4) was larger than during dexmedetomidine-induced unconsciousness (power, −0.4 dB±3.1). This means that the amplitude of slow oscillations during propofol-induced unconsciousness (PM) was approximately 4.8-fold larger than dexmedetomidine-induced unconsciousness slow oscillations. Similarly, during propofol-induced unconsciousness (PM), the electroencephalogram exhibited frontal alpha oscillations (power, 1.1 dB±4.5), which were also larger than the dex-spindles (power, −10.8 dB±3.6). This means that the amplitude of alpha oscillations during propofol-induced unconsciousness (PM) was approximately 3.9-fold larger than dexmedetomidine-induced unconsciousness spindle oscillations. Our results show that the spindle-like electroencephalogram pattern induced by dexmedetomidine is distinct from the propofol-induced frontal alpha oscillations. Also, amplitude wise, propofol-induced unconsciousness (PM) slow oscillations were much larger than dexmedetomidine-induced unconsciousness slow oscillations.

Dexmedetomidine Vs. Baseline Coherence

Figures 12B, 12C:
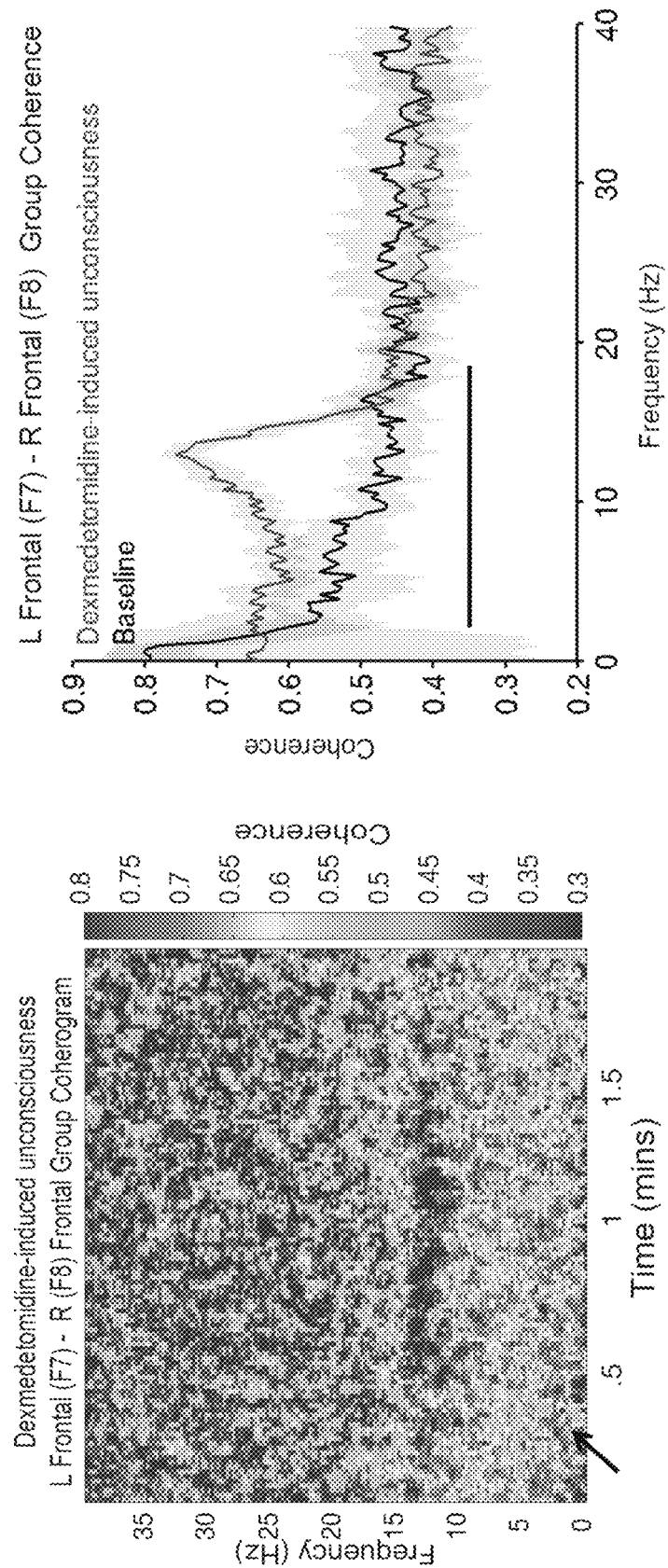
FIG. 12B is a group level coherogram of dexmedetomidine-induced unconsciousness, as described in Example 1.
FIG. 12C shows the coherence of dexmedetomidine baseline vs. dexmedetomidine-induced unconsciousness, as described in Example 1.

Differences were observed in the coherogram that were induced by dexmedetomidine. Dexmedetomidine-induced unconsciousness was characterized by an increase in coherence across a frequency range of 1-15 Hz (FIGS. 12A and 12B) and a decrease in 0.1-1 Hz coherence (solid arrow, FIG. 12B). We next compared the EEG coherence during dexmedetomidine-induced unconsciousness to baseline, and found significant differences in coherence across frequencies between 2.4 and 18.8 Hz, with a coherence peak (peak frequency, 13.4 Hz±0.8, peak coherence, 0.78±0.08) consistent with the dex-spindle (FIG. 12C; 2.4-18.8 Hz; P<0.001, TGTC). Our results show that compared to the awake-state, dexmedetomidine-induced unconsciousness was characterized by dex-spindles that were significantly more coherent and a non-significant decrease in slow oscillation coherence.

Propofol Vs. Baseline Coherence

Figures 13A, 13B, 13C:
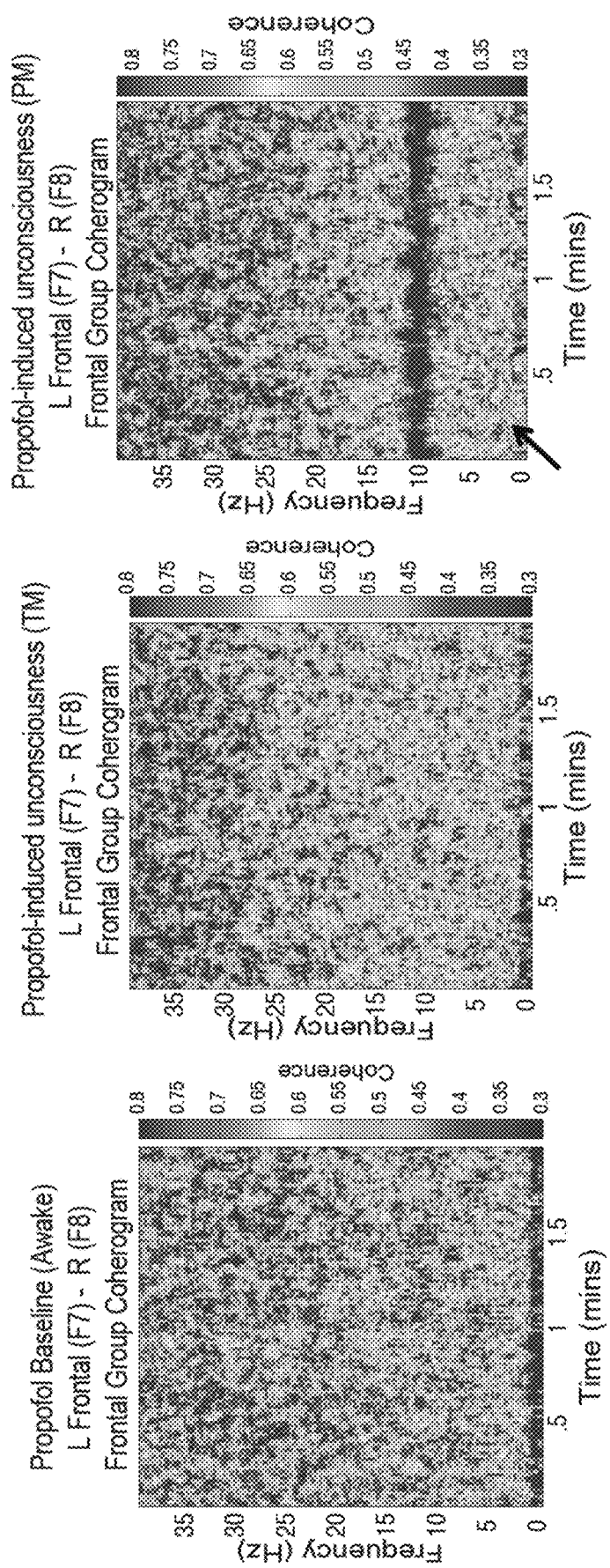
FIG. 13A is a group level coherogram of propofol baseline, as described in Example 1.
FIG. 13B is a group level coherogram of propofol-induced unconsciousness (TM), as described in Example 1.
FIG. 13C is a group level coherogram of propofol-induced unconsciousness (PM), as described in Example 1.
Figures 13D, 13E:
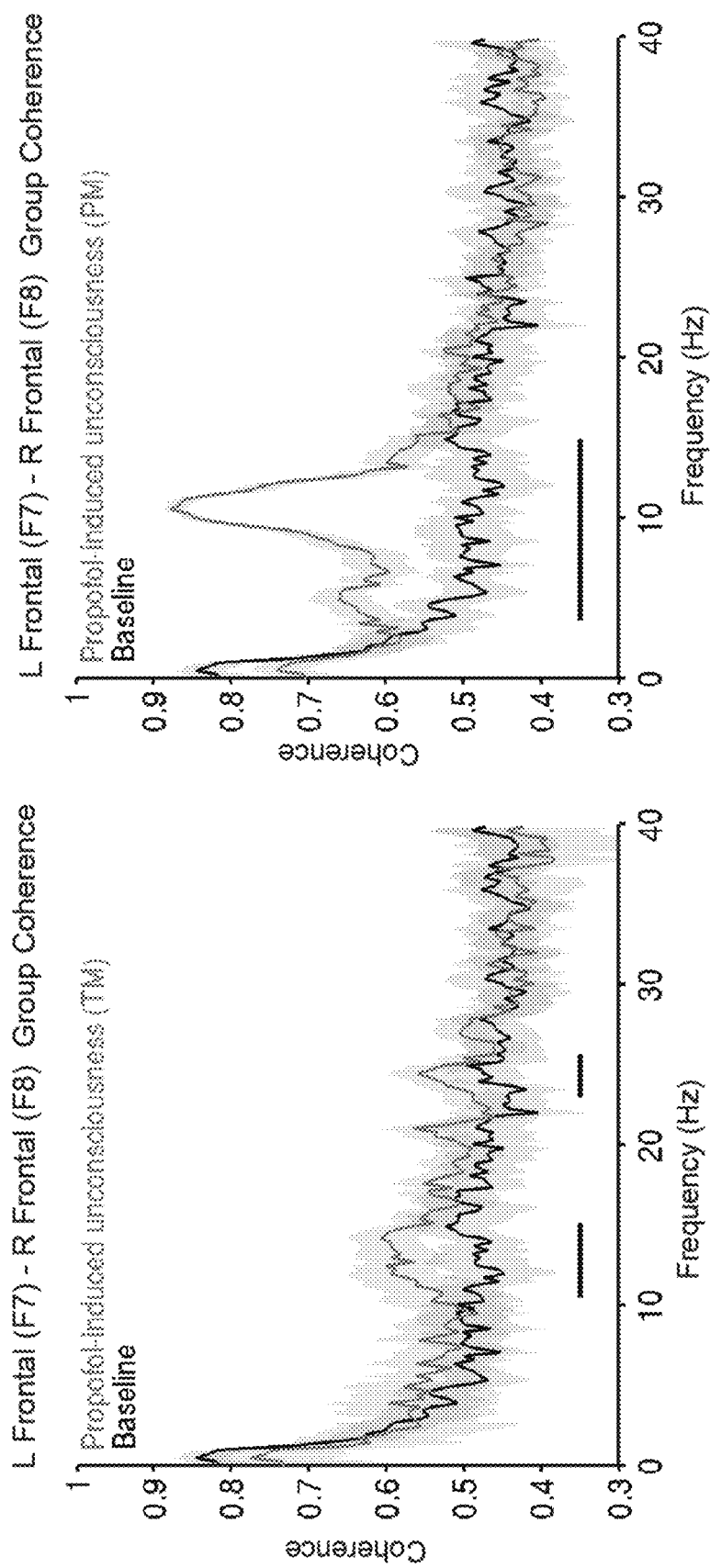
FIG. 13D shows the coherence of propofol baseline vs. propofol-induced unconsciousness (TM), as described in Example 1.
FIG. 13E shows the coherence of propofol baseline vs. propofol-induced unconsciousness (PM), as described in Example 1.

Compared to baseline, differences in the coherogram during propofol-induced unconsciousness (TM) and propofol-induced unconsciousness (PM) were also observed. Propofol induced unconsciousness (TM) was characterized by a broad (~1-25 Hz) increase in coherence on the coherogram. Propofol-induced unconsciousness (PM) was characterized by a narrow band of alpha oscillation coherence centered at ~10 Hz (FIGS. 13A, 13B, and 13C) and a decrease in 0.1-1 Hz coherence (solid arrow, FIG. 13C). The coherence during propofol-induced unconsciousness (TM) and propofol-induced unconsciousness (PM) were then compared to the baseline and to each other. Oscillations induced during propofol-induced unconsciousness (TM) were coherent in beta and gamma frequency ranges (FIG. 13D, 10.7-15.4 Hz, 17.3-25.9 Hz; P<0.0003, TGTC). Notably, during propofol-induced unconsciousness (PM), there was a distinct alpha oscillation coherence peak (peak frequency, 10.8 Hz±0.9, peak coherence, 0.89±0.05) and significant increase in coherence within theta and alpha frequencies (FIG. 13E; 3.9-15.1 Hz; P<0.0003, TGTC). Also, propofol-induced unconsciousness (PM) was characterized by a non-significant decrease slow oscillation coherence.

Figure 13F:
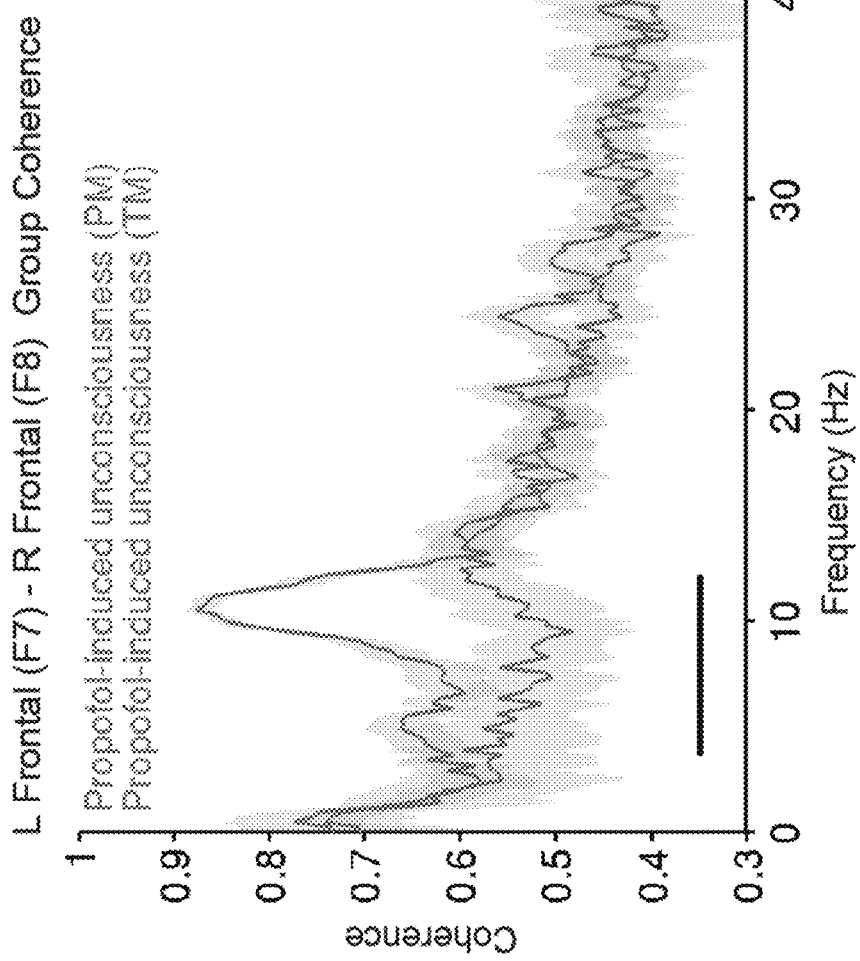
FIG. 13F shows the coherence of propofol-induced unconsciousness (TM) vs. propofol-induced unconsciousness (PM), as described in Example 1.

Propofol-induced unconsciousness (PM) oscillations were coherent in theta and alpha frequency ranges (FIG. 13F; 3.9 Hz-12.5 Hz; P<0.0003, TGTS). These results are consistent with previous reports that coherent frontal beta/gamma oscillations and alpha oscillations are exhibited during propofol-induced unconsciousness (TM) and propofol-induced unconsciousness (PM), respectively.

Dexmedetomidine Vs. Propofol Coherence

Figures 15A, 15B:
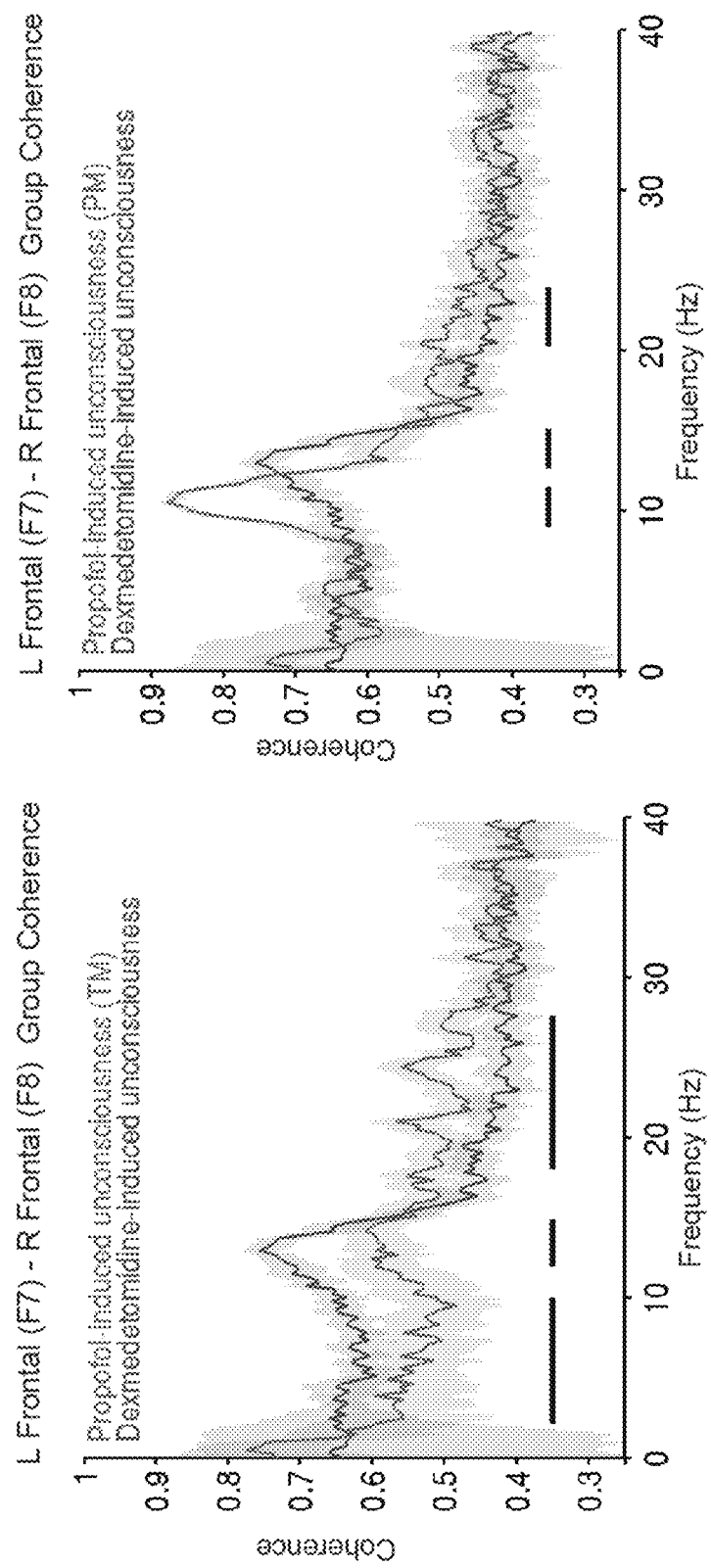
FIG. 15A shows the coherence of dexmedetomidine-induced unconsciousness vs. propofol-induced unconsciousness (TM), as described in Example 1.
FIG. 15B shows the coherence of dexmedetomidine-induced unconsciousness vs. propofol-induced unconsciousness (PM), as described in Example 1.

Coherence patterns during dexmedetomidine sedation were then compared to both propofol-induced unconsciousness EEG epochs. Compared to propofol-induced unconsciousness (TM), during dexmedetomidine-induced unconsciousness, coherence was larger in the delta, theta, spindle frequency bands with a coherent dex-spindle peak (FIG. 15A; 2.4-10.3 Hz, 12.2-15.3 Hz; P<0.0005, TGTC). Coherence was larger during propofol-induced unconsciousness (TM) compared to dexmedetomidine-induced unconsciousness within beta/gamma frequency bands (FIG. 15A; 17.3-25.9 Hz, P<0.0005, TGTC). Next, the coherence patterns during dexmedetomidine-induced unconsciousness were compared to propofol-induced unconsciousness (PM). We found that dex-spindles and propofol-induced frontal alpha oscillations were distinct in terms of peak coherence and frequency (FIG. 15B). Coherence during propofol-induced unconsciousness (PM) was significantly larger at frequencies surrounding the alpha oscillation peak and at a narrow gamma band (FIG. 15B; 9.3-11.7 Hz, 19.5-26.9 Hz; P<0.0005, TGTC). Coherence during dexmedetomidine-induced unconsciousness was significantly larger at frequencies surrounding the dex-spindle peak (FIG. 15B; 12.9-15.4 Hz; P<0.0005, TGTC). The results using coherence analysis show again that the spindle-like EEG pattern induced by dexmedetomidine is distinct from the propofol-induced frontal alpha oscillations.

Discussion

Although propofol- and dexmedetomidine-induced EEG signatures appear grossly similar, the analysis described herein identifies distinct differences in the power spectrum and coherence that likely relate to the specific underlying mechanisms and clinical properties of these drugs. The findings are briefly summarized as follows:

(i) Similar to sleep spindles, dexmedetomidine-induced unconsciousness is characterized by spindles whose maximum power and coherence occur at ~13 Hz. These dex-spindles were different in both the power spectrum and coherence from propofol-induced alpha and beta oscillations. Alpha oscillations during propofol-induced unconsciousness (PM) were more coherent, and were approximately 3.9-fold larger in amplitude than dexmedetomidine-induced unconsciousness spindle oscillations.

(ii) Both dexmedetomidine sedation and propofol-induced unconsciousness are associated with slow oscillations characterized by increased power and reduced coherence at frequencies <1 Hz. However, the amplitude of slow oscillations during propofol-induced unconsciousness (PM), which is synonymous with general anesthesia, was much larger than those observed during both dexmedetomidine-induced unconsciousness and propofol-induced unconsciousness (TM).

Slow oscillations have been proposed as a shared mechanism for unconsciousness during sleep and anesthesia. Since dexmedetomidine acts through neural circuits involved in the generation of NREM sleep, dexmedetomidine-induced slow waves are likely similar in nature to sleep slow waves. Both sleep slow waves and propofol-induced slow oscillations appear to have a local or spatially-asynchronous character that make them incoherent across different cortical regions. This is consistent with the finding that slow oscillation coherence decreases during both dexmedetomidine sedation and propofol-induced unconsciousness At the neuronal level, slow oscillations are associated with an alternation between "ON" states where neurons are able to fire, and "OFF" states where neurons are silent. In sleep and under the alpha2 agonist xylazine, these "OFF" periods appear to be relatively brief, occupying a fraction of the slow oscillation period. In contrast, under propofol, these OFF periods are prolonged, occupying the majority of the slow oscillation period. This prolonged state of neuronal silence could explain why propofol produces a deeper state of unconsciousness from which patients cannot be aroused, compared to sleep or dexmedetomidine-induced sedation, where patients can be aroused to consciousness. Herein, we observed that propofol-induced slow oscillations were almost an order of magnitude larger than those during dexmedetomidine sedation. These much larger slow oscillations may explain why propofol OFF states appear prolonged compared to sleep or xylazine anesthesia. We speculate that the size of the propofol-induced slow oscillation, and the duration of the associated OFF states, could come from propofol's actions at GABAergic interneurons, which could help support larger slow waves and deeper levels of hyperpolarization required to sustain OFF states. These results also suggest that the power or amplitude of slow oscillations could be used to distinguish between propofol-induced unconsciousness and sleep or sleep-like states such as dexmedetomidine-induced sedation.

The dex-spindle pattern described herein has a frequency range and transient time-domain morphology that appears similar to sleep spindles. This suggests that the same thalamocortical circuit underlying sleep spindles could generate dex-spindles. Biophysical models have also established a thalamocortical basis for propofol-induced frontal alpha oscillations. This frontal alpha EEG activity is thought to contribute to alterations in consciousness by drastically restricting communication within frontal thalamocortical circuits from a wide to a narrow frequency band. They may also signify a change in anterior-posterior cortical coupling. These results show that propofol-induced frontal alpha waves are larger and more coherent than dex-spindles, which may also explain why propofol is able to induce deeper levels of sedation and unconsciousness than dexmedetomidine. The analysis described herein suggests that these drugs are acting differently within the same underlying thalamocortical system. These differences may relate to the drugs underlying molecular and neuronal mechanisms. In particular, propofol's traveling peak dynamics, as well as its highly coherent frontal ~10 Hz alpha oscillation, appear to be generated by enhanced GABA inhibition at cortical and thalamic interneurons. Meanwhile, dexmedetomidine appears to act through endogenous NREM sleep circuits, which may explain why dex-spindles appear similar in morphology to sleep spindles. Because Laplacian-referenced EEGs, which favor local signals over global signals, were analyzed, it is unlikely that the observed alpha- and spindle-band coherences are due to a broad common-mode signal.

Distinct differences in the properties of slow oscillations and thalamocortical oscillations induced by dexmedetomidine and propofol were demonstrated. Moreover, based on the present analysis and discussion, it is likely that these differences in EEG dynamics are directly related to underling differences in molecular and neural circuit mechanisms. While the EEG has historically been viewed within anesthesiology as a "black box," the present analysis suggests a powerful alternative: the EEG could be utilized to provide an assessment of the state of consciousness of a subject or the likelihood that a subject can be aroused by an external stimulus. The EEG signatures described here can be readily computed and displayed in real-time, suggesting that it is possible to display these dynamics in a straightforward way similar to other physiological signals.

In summary, the practice of anesthesiology involves the direct pharmacological manipulation of the central nervous system to achieve the required combination of unconsciousness, amnesia, analgesia, and immobility with maintenance of physiological stability that define general anesthesia. Recent advances in neuroscience research methods are helping to refine the understanding of the neural circuit mechanisms of anesthesia-induced unconsciousness. Nonetheless, despite major advances in identifying common molecular and pharmacological principles that underlie anesthetic drugs, it is not yet apparent how actions at different molecular targets affect large-scale neural dynamics to produce unconsciousness. At the molecular level, general anesthetics modulate ion-channels in key regions of the brain and spinal cord to disrupt synaptic transmission, giving rise to distinct electroencephalogram (EEG) signatures. These ion-channels may include $\gamma$-Aminobutyric acid (GABA$_A$), glutamate, icotinic acetylcholine, glycine, potassium and serotonin.

Most studies have focused on a deep steady state of general anesthesia and have not used a systematic behavioral measure to track the transition into unconsciousness nor the probability of arousing a subject from unconsciousness with an external stimulus. This steady-state approach cannot distinguish between EEG patterns that are characteristic of a deeply anesthetized brain and those that arise at the onset of unconsciousness. For example, unconsciousness can occur in tens of seconds, but many neurophysiological features continue to fluctuate for minutes after induction and are highly variable between different levels of general anesthesia. As such, the relationships between stereotypical EEG patterns manifested by general anesthetics and altered arousal remain poorly understood. Therefore, identifying the specific dynamics associated with arousal from unconsciousness requires an examination of the transition out of unconsciousness, linking neurophysiology with behavioral measures.

In one approach presented above, the size of EEG slow and thalamocortical oscillations, as well as the frequency of thalamocortical oscillations, could be used to provide information relating to the likelihood of arousing a patient from unconsciousness with an external stimulus. In particular, in comparing propofol-induced unconsciousness (PM), in which subjects cannot be aroused to consciousness by external stimuli ("unarousable"), with either propofol-induced unconsciousness (TM) or dexmedetomidine-induced unconsciousness, in which subjects can be aroused to consciousness by external stimuli ("arousable"), the approach presented above suggests that the size of slow, alpha, beta, and spindle oscillations can be used to assess the likelihood of arousing a patient from unconsciousness with an external stimulus. The size of the oscillations could be quantified in a number of ways, including power in different frequency bands, or the amplitude or magnitude at specific frequencies, for example.

Therefore, in accordance with the present disclosure, coherent and non-coherent slow or low-frequency oscillations, resulting from anesthesia-induced sedation and unconsciousness, may provide systems and methods with indicators, which are rigorously linked to basic neurophysiology of anesthesia-induced unconsciousness, for use in tracking or monitoring sedation or unconsciousness. Using measures of brain coherence and synchrony, and possibly other characteristics or indicators, systems and methods may be used to distinguish between sedative states of consciousness, where patients can be aroused by external stimuli, and general anesthetic states of consciousness, where patients cannot be aroused by external stimuli. In addition, measures of brain coherence and synchrony, and possibly other characteristics or indicators, may be used in systems and methods configured to predict, for example, when patients may emerge from general anesthesia, or predict when patients may enter a state of unconsciousness during induction of general anesthesia. Similarly, systems and methods in accordance with the present disclosure may also be used to determine when a patient's brain state and brain response to sedative drugs is changing during long-term sedation within an intensive care unit, or determine when a patient's brain state is changing due to metabolic or infectious disease states during intensive care.

As described, anesthesia-induced unconsciousness may be associated with two specific states of brain dynamics. The first is a highly synchronous oscillation in the alpha or spindle band involving the thalamus and frontal cortex. The second consists of asynchronous <1 Hz slow oscillations. These oscillations generate large electromagnetic fields that can be recorded at the scalp in the form of electroencephalogram. The coherence and coherogram methods described here provide a means of identifying these thalamocortical and asynchronous slow oscillations. In particular, coherence or coherogram can be used to improve monitoring and quantification of these unconsciousness-related brain dynamics.

Specifically, it can be difficult at times to clearly identify the frontal alpha or spindle oscillations, which are anesthesia-induced thalamocortical oscillations associated with the unconscious state, just from looking at the spectrogram. The visibility of these oscillations can depend on how the spectrogram is scaled, and the structure of oscillations in the beta, alpha, theta, delta, and slow bands can be difficult to discern. Thus, the coherence and coherogram information, in accordance with the present disclosure, provide a clearer view of the frontal alpha and spindle oscillations that reflect thalamocortical oscillations associated with the unconscious state.

In addition, it can also be difficult at times to clearly identify the slow oscillations induced by anesthetic drugs just from looking at the spectrum or spectrogram. This is because low-frequency power, less than approximately 1 Hz, may generally be present in the baseline conscious state. Anesthesia-induced slow oscillations associated with unconsciousness, as described, are asynchronous across different areas of the cerebral cortex. Furthermore, coherence provides a means to quantify the extent to which oscillations are synchronized. Thus, the coherence and coherogram provide a means to more clearly identify anesthesia-induced asynchronous slow oscillations associated with the unconscious state.

Thus, a clinician could observe the size of EEG slow oscillations, the size of thalamocortical oscillations, and/or the frequency of thalamocortical oscillations, and assess the likelihood of arousing the subject with an external stimulus. Changes in the size of EEG slow oscillations, the size of thalamocortical oscillations, and/or the frequency of thalamocortical oscillations could indicate changes in the patient's state of arousal or consciousness. In such cases, the clinician could adjust the strategy or timeline for arousing the patient. If the clinician were interested in having the patient recover consciousness, or have the patient go to a state where they could be more easily aroused or more easily recover consciousness, or one where the patient is conscious but sedated, the coherence could be used to help achieve these states as well.

This novel approach may shift the focus of anesthesiology towards understanding the neurophysiology and neuroanatomical basis of brain states created by anesthetic drugs, and may position anesthesiologists to make new and important contributions to clinical practice and neuroscience research by directly furthering knowledge of the neural bases of sleep, arousal and pathological states.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the disclosures described herein can be embodied within a form that does not provide all of the features and benefits set forth herein, as some features can be used or practiced separately from others. The scope of certain disclosures disclosed herein is indicated by the appended claims rather than by the foregoing description. All changes which come within the meaning and range of equivalency of the claims are to be embraced within their scope.

The invention claimed is:

1. A system for monitoring a patient suspected of experiencing a state of unconsciousness, the system comprising:
at least one sensor configured to acquire physiological data from the patient;
at least one processor configured to:
receive the physiological data from the at least one sensor;
separate, from the physiological data, a plurality of electroencephalogram signals;
determine, from the plurality of electroencephalogram signals, at least one of frequency information and amplitude information;
identify, using the at least one of the frequency information and the amplitude information, spatiotemporal signatures indicative of a likelihood of arousing the patient to consciousness by applying an external stimulus; and
generate a report indicating the likelihood of arousing the patient to consciousness by applying the external stimulus; and
at least one stimulator configured to apply the external stimulus to the patient.

2. The system of claim 1, wherein the at least one of frequency information and amplitude information is amplitude information for electroencephalogram slow oscillations.

3. The system of claim 1, wherein the processor is configured to assemble the physiological data into sets of time-series data and transform each set of time-series data into a spectrogram to determine the likelihood of arousing the patient to consciousness by applying the external stimulus.

4. The system of claim 1, wherein the processor is configured to perform a phase analysis on the plurality of electroencephalogram signals to determine the likelihood of arousing the patient to consciousness by applying the external stimulus.

5. The system of claim 1, wherein the processor is configured to perform a coherence analysis on the plurality of electroencephalogram signals to determine the likelihood of arousing the patient to consciousness by applying the external stimulus.

6. The system of claim 1, wherein the state of unconsciousness is suspected of having been induced by at least one drug having anesthetic properties, the at least one drug having anesthetic properties selected from the group consisting of Propofol, Etomidate, Barbiturates, Thiopental, Pentobarbital, Phenobarbital, Methohexital, Benzodiazepines, Midazolam, Diazepam, Lorazepam, Dexmedetomidine, Ketamine, Sevoflurane, Isoflurane, Desflurane, Remifentanil, Fentanyl, Sufentanil, Alfentanil, and combinations thereof.

7. The system of claim 1, wherein the external stimulus is an auditory stimulus.

8. A method for monitoring a patient suspected of experiencing a state of unconsciousness, the method comprising:
positioning at least one sensor and the patient relative to one another, the at least one sensor configured to acquire physiological data from the patient;
receiving, at a processor, the physiological data from the at least one sensor;
identifying, using the processor and the physiological data, a plurality of electroencephalogram signals;
determining, using the processor and the plurality of electroencephalogram signals, at least one of frequency information and amplitude information;
identifying, using the processor and at least one of the frequency information and the amplitude information, spatiotemporal signatures indicative of a likelihood of arousing the patient to consciousness by applying an external stimulus;
generating a report indicating the likelihood of arousing the patient by applying the external stimulus; and
applying the external stimulus to the patient.

9. The method of claim 8, wherein the at least one of frequency information and amplitude information is amplitude information for electroencephalogram slow oscillations.

10. The method of claim 8, the method further comprising transforming the physiological data into a spectrogram and analyzing the spectrogram to determine the likelihood of arousing the patient to consciousness by applying the external stimulus.

11. The method of claim 8, the method further comprising performing a phase analysis on the plurality of electroencephalogram signals to determine the likelihood of arousing the patient to consciousness by applying the external stimulus.

12. The method of claim 8, the method further comprising performing a coherence analysis on the plurality of electroencephalogram signals to determine the likelihood of arousing the patient to consciousness by applying the external stimulus.

13. The method of claim 8, the method further comprising inducing the state of unconsciousness by administering at least one drug having anesthetic properties, the at least one drug having anesthetic properties selected from the group consisting of Propofol, Etomidate, Barbiturates, Thiopental, Pentobarbital, Phenobarbital, Methohexital, Benzodiazepines, Midazolam, Diazepam, Lorazepam, Dexmedetomidine, Ketamine, Sevoflurane, Isoflurane, Desflurane, Remifentanil, Fentanyl, Sufentanil, Alfentanil, and combinations thereof.

14. The method of claim 8, wherein the external stimulus is an auditory stimulus.

\* \* \* \* \*

UNITED STATES PATENT AND TRADEMARK OFFICE
CERTIFICATE OF CORRECTION

PATENT NO. : 11,786,132 B2
APPLICATION NO. : 16/657194
DATED : October 17, 2023
INVENTOR(S) : Patrick L. Purdon et al.

It is certified that error appears in the above-identified patent and that said Letters Patent is hereby corrected as shown below:

In the Specification

Column 15, Line 8, "the a range" should be --the α range--.

Signed and Sealed this
Second Day of January, 2024

Katherine Kelly Vidal
*Director of the United States Patent and Trademark Office*